US012083521B2

United States Patent
Schulz et al.

(10) Patent No.: US 12,083,521 B2
(45) Date of Patent: Sep. 10, 2024

(54) SAMPLE CARTRIDGE FOR INCUBATING AND/OR ANALYZING A DISPERSION OF PARTICLES, CELLS OR DROPLETS

(71) Applicant: BLINK AG, Jena (DE)

(72) Inventors: Torsten Schulz, Jena (DE); Eugen Ermantraut, Jena (DE); Katrin Steinmetzer, Jena (DE); Alrik Wolff, Weimar (DE)

(73) Assignee: BLINK AG, Jena (DE)

( * ) Notice: Subject to any disclaimer, the term of this patent is extended or adjusted under 35 U.S.C. 154(b) by 334 days.

(21) Appl. No.: 16/626,647

(22) PCT Filed: Jul. 2, 2018

(86) PCT No.: PCT/EP2018/067819
§ 371 (c)(1),
(2) Date: Dec. 26, 2019

(87) PCT Pub. No.: WO2019/002622
PCT Pub. Date: Jan. 3, 2019

(65) Prior Publication Data
US 2020/0156077 A1 May 21, 2020

(30) Foreign Application Priority Data
Jun. 30, 2017 (EP) .................................... 17179194

(51) Int. Cl.
*B01F 35/513* (2022.01)
*B01F 23/411* (2022.01)
(Continued)

(52) U.S. Cl.
CPC .............. *B01L 7/52* (2013.01); *B01F 23/4111* (2022.01); *B01F 31/20* (2022.01); *B01F 35/513* (2022.01);
(Continued)

(58) Field of Classification Search
CPC .............. B01F 11/0005; B01F 11/0065; B01F 11/0266; B01F 15/0085; B01F 3/0807;
(Continued)

(56) References Cited

U.S. PATENT DOCUMENTS

2002/0086417 A1 7/2002 Chen
2009/0074823 A1 3/2009 Takakura
(Continued)

FOREIGN PATENT DOCUMENTS

EP 2241314 A1 10/2010
WO 94014068 A1 6/1994

OTHER PUBLICATIONS

Tong, Weijun, Xiaoxue Song and Changyou Gao entitled "Layer-by-layer assembly of microcapsules and their biomedical applications," Chem. Soc. Rev 41:6103-6124, 2012.

*Primary Examiner* — Lydia Edwards
(74) *Attorney, Agent, or Firm* — SALIWANCHIK, LLOYD & EISENSCHENK

(57) ABSTRACT

The present invention relates to a sample cartridge for incubating and/or analyzing a dispersion of particles, cells or droplets and/or for performing biochemical reactions with or in such dispersion. The present invention furthermore relates to a device for incubating a dispersion of particles, cells or droplets and/or for performing a biochemical reaction therewith. Moreover, the present invention also relates to the use of a sample cartridge or of a device for generating and/or processing a dispersion of particles, cells or droplets. Moreover, the present invention relates to a method of processing a dispersion of particles, cells or droplets. Furthermore, the present invention relates to a method of generating a dispersion of droplets and to a method of generating a dispersion of solid or semi-solid particles.

19 Claims, 12 Drawing Sheets

(51) Int. Cl.
  *B01F 31/20*   (2022.01)
  *B01L 3/00*    (2006.01)
  *B01L 7/00*    (2006.01)
  *B01L 99/00*   (2010.01)
  *C12M 1/00*    (2006.01)
  *C12M 1/34*    (2006.01)
  *G01N 15/00*   (2024.01)
  *G01N 15/1433* (2024.01)
  *G01N 15/14*   (2006.01)

(52) U.S. Cl.
  CPC ......... *B01L 3/502776* (2013.01); *B01L 3/505* (2013.01); *C12M 41/14* (2013.01); *G01N 15/1433* (2024.01); *B01L 2200/0636* (2013.01); *B01L 2200/0684* (2013.01); *B01L 2300/042* (2013.01); *B01L 2300/0681* (2013.01); *B01L 2300/0832* (2013.01); *B01L 2300/1822* (2013.01); *B01L 2400/0409* (2013.01); *B01L 2400/0457* (2013.01); *B01L 2400/0481* (2013.01); *B01L 2400/049* (2013.01); *B01L 2400/0655* (2013.01); *G01N 2015/1493* (2013.01)

(58) Field of Classification Search
  CPC ........... B01F 3/0819; B01L 2200/0631; B01L 2200/0636; B01L 2200/0684; B01L 2300/042; B01L 2300/0681; B01L 2300/0832; B01L 2300/1822; B01L 2400/0409; B01L 2400/0457; B01L 2400/0481; B01L 2400/049; B01L 2400/0655; B01L 3/502776; B01L 3/505; B01L 7/52; C12M 41/14; G01N 15/1463; G01N 2015/1493; G01N 2035/00099; G01N 2035/00366
  See application file for complete search history.

(56) References Cited

U.S. PATENT DOCUMENTS

| | | |
|---|---|---|
| 2010/0317093 A1 | 12/2010 | Turewicz |
| 2012/0156799 A1 | 6/2012 | Komarek |
| 2014/0038272 A1 | 2/2014 | Ririe |
| 2015/0096358 A1 | 4/2015 | Putnam |
| 2016/0129437 A1* | 5/2016 | Kayyem ................. B01L 7/525 |
| | | 204/600 |
| 2017/0182493 A1 | 6/2017 | Perroud |

* cited by examiner

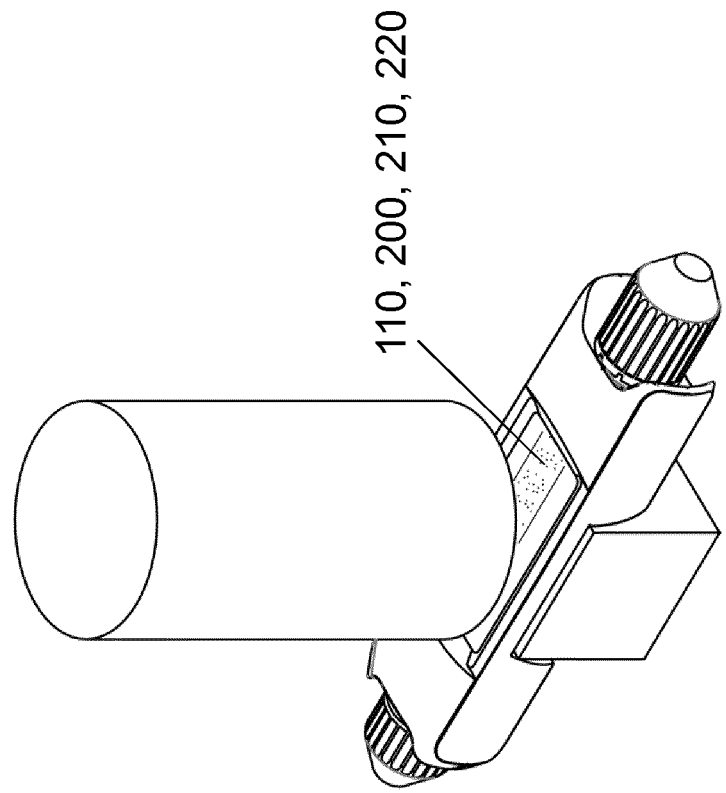
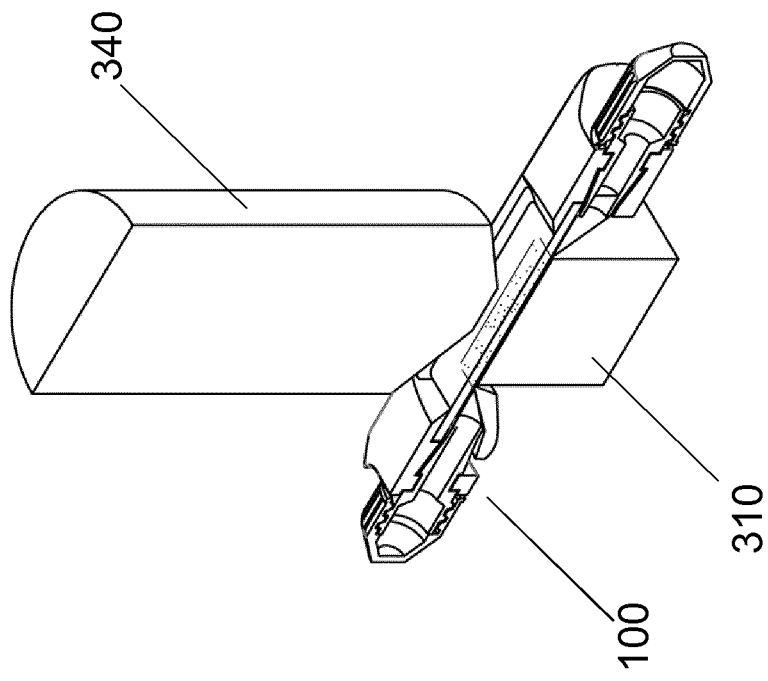
Figure 5

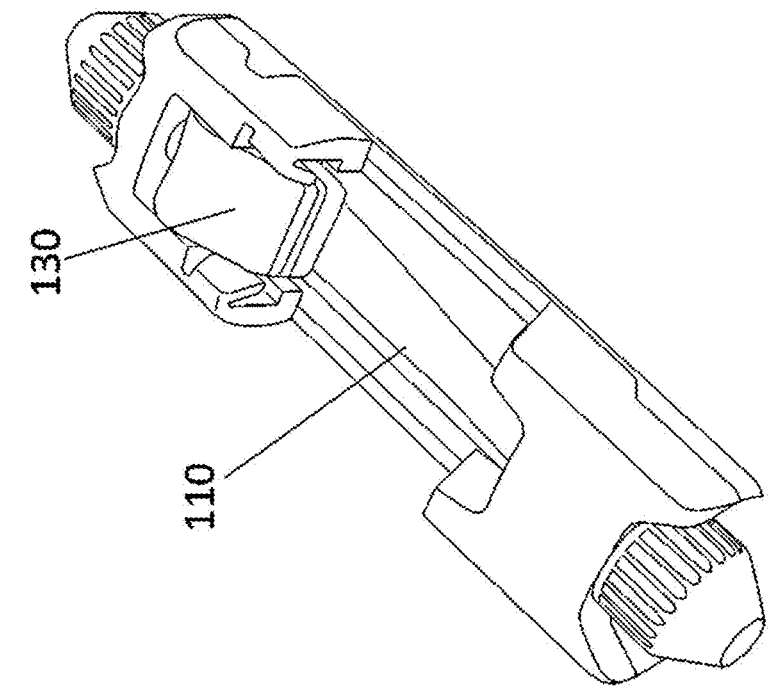
cartridge with clamp in closed position, tube has a circular cross section at one end and a flat, non-circular cross section at the other end
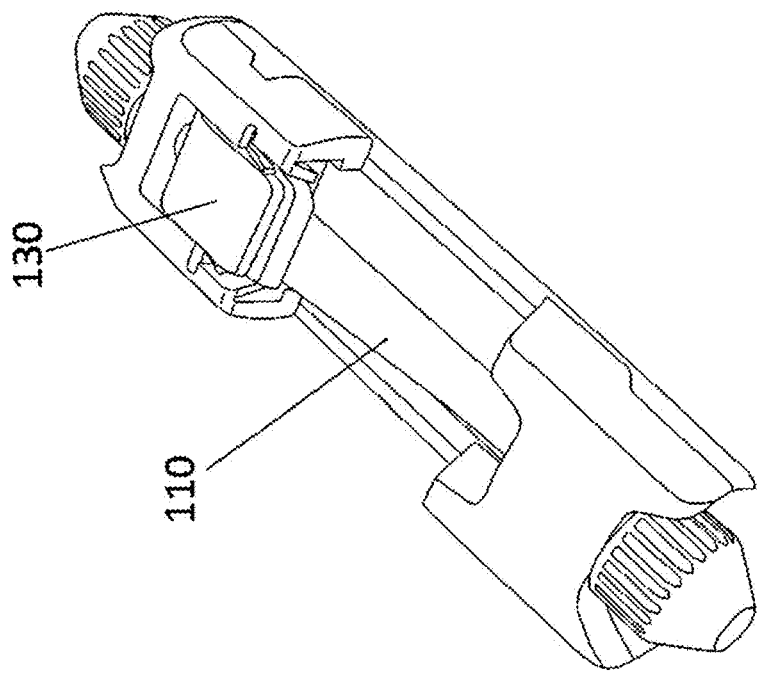
cartridge with clamp in open position, tube as a circular cross section
Figure 8

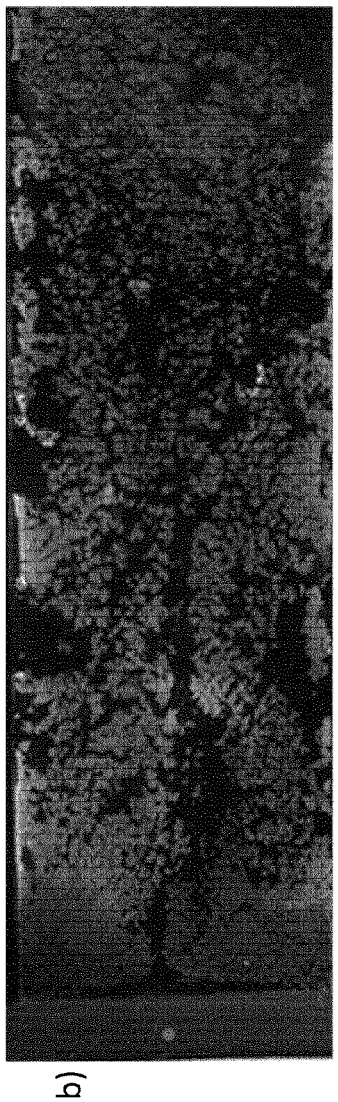
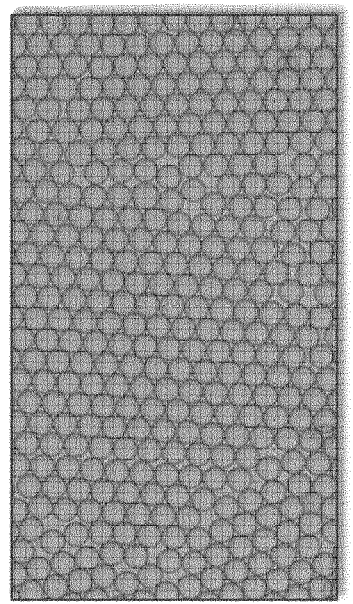
a) Light transmission image of spread particles (particle diameter 35μm)
b) Fluorescence image of compressed tube with spread particles after thermocycling (size of image 2X6 cm), at the left the clamped area is visible
Figure 11

SAMPLE CARTRIDGE FOR INCUBATING AND/OR ANALYZING A DISPERSION OF PARTICLES, CELLS OR DROPLETS

CROSS REFERENCE TO RELATED APPLICATIONS

This application is a National Stage Application of International Application Number PCT/EP2018/067819, filed Jul. 2, 2018; which claims priority to European Patent Application No. 17179194.0, filed Jun. 30, 2017.

The present invention relates to a sample cartridge for incubating and/or analyzing a dispersion of particles, cells or droplets and/or for performing biochemical reactions with or in such dispersion. The present invention furthermore relates to a device for incubating a dispersion of particles, cells or droplets and/or for performing a biochemical reaction therewith. Moreover, the present invention also relates to the use of a sample cartridge for generating and/or processing a dispersion of particles, cells or droplets. Moreover, the present invention relates to a method of processing a dispersion of particles, cells or droplets.

Many biological and chemical test procedures or processes require the incubation of suspensions of particles or emulsions of droplets at one or several defined temperatures and for one or several defined periods of time. In order to ensure comparable results, the particles or droplets need to be exposed to one or several precisely defined temperatures. This can be achieved by continuous or sequential movement of the sample or by reducing the cross-section of the reaction space. A flat reaction chamber that is in close contact with the element controlling and defining the temperature allows for a rapid heat transfer which is particularly useful in the context of temperature cycling or fast heating or cooling steps which may be required by certain assay processes. However, such flat chambers are assembled from different parts and are typically sealed at the edges. This results in complex assembly procedures, high costs and assembly artifacts that may have a detrimental effect on the performance of such assembled reaction chambers/cuvettes. One possible detrimental effect relates to the formation of gas bubbles forming at the edges of a reaction chamber during the filling of such reaction chamber. Gas bubbles may lead to a temperature inhomogeneity and may adversely affect the optical observation of any process taking place within the reaction chamber. Another possible detrimental effect is related to the relative rigid design of the chamber, which may result in a non-optimal heat exchange between a heater/cooler and the chamber. This is mainly due to remaining small air gaps between the surfaces. It is therefore desirable to have a chamber geometry reducing the risk of such artifacts and yet providing for an optimum heat transfer, temperature homogeneity and allowing an optical observation of the reaction space.

In the state of the art, different devices have been described in order to facilitate the incubation of liquids. Traditionally, the simplest is to use a standard micro reaction vial and allowing it to adjust to the defined temperature over an extended period of time. Many different kinds of microfabricated chambers have been used in order to improve mixing efficiency and temperature homogeneity. For example EP 0 891 811 A1 describes a method and apparatus for mixing a thin film of fluid. The device employs a mixing mechanism which induces mixing within the fluid chamber formed by two opposing surfaces as a result of which the liquid in the fluid chamber is agitated. A similar set up involving a microchip with immobilized probes is described in FR 2803225. WO 03/015923 describes microfluidic devices with means enabling the movement of liquids in a low volume, low aspect ratio microfluidic chamber. All of the aforementioned devices represent micromechanically fabricated microsystems with micro channels built from different parts that are assembled to have at least two different surfaces. WO 2007/051861 discloses a device and method for the detection of particles which comprises a reaction chamber formed within a chamber body between a first surface and an oppositely located second surface. The device furthermore comprises one or more displaces providing for the displacement of label and liquid within the chamber. Digital techniques based on droplet emulsions have become an important approach in bioanalytics and thus new tools and methods are required in order to facilitate processing of emulsified samples. Such techniques are technically similar to processing of cells or beads and thus an improved solution would benefit the processing all this types of analytes.

There is a need in the art for a reaction chamber reducing the risk of artifact formation, such as uncontrolled formation of gas bubbles and that allows for optimum heat transfer, temperature homogeneity and optical observation of the sample within the reaction chamber.

In a first aspect, the present invention relates to a sample cartridge (100) for incubating and/or analyzing a dispersion (200) of particles, cells or droplets, in particular a suspension (210) of particles or cells, or an emulsion (220) of droplets, and/or for performing biochemical reactions with or in such dispersion, said cartridge comprising:
  a deformable transparent tube (110) having:
    two oppositely located open ends (111, 112) serving as an inlet and an outlet, respectively,
  said tube being adapted to receive a dispersion of particles, cells or droplets, in particular a suspension of particles or cells, or an emulsion of droplets, in an interior space (113) of said tube, said interior space being lined by one (114''') or several walls (114, 114', 114'') of said tube, wherein the tube is configured such that the interior space of said tube, when having received said suspension or emulsion or dispersion, has a circular or oval cross-section, and such that the interior space, when the tube is pressed against a surface, has a flat, noncircular cross-section,
said cartridge further comprising means to withhold (120) said particles, cells or droplets in said deformable transparent tube, said means to withhold said particles being located at one or both ends of said tube, said means to withhold preferably being a filter, a membrane, a grid, a mesh, a sieve or other structure allowing the passage of liquid through it whilst retaining said particles.
  In one embodiment, said deformable transparent tube has:
    a single wall (114''');
  wherein said interior space (113) is lined by said single wall.
  In one embodiment, the sample cartridge further comprises:
    means to reversibly close and seal (130) said deformable transparent tube at one or both of said oppositely located ends (111, 112), wherein, preferably said means to reversibly seal is a clamp or, in the case of sealing at both ends, a pair of clamps located at said opposite ends.
  In one embodiment, the sample cartridge further comprises:

a mounting frame (140) connected to and holding said tube at said oppositely located ends of said tube and configured to allow addition of material, e.g. liquid or solid or a mixture thereof, to said interior space of said tube via one of said ends serving as inlet, and/or removal of material, e.g. liquid or solid or a mixture thereof, from said interior space of said tube via one of said ends serving as an outlet.

In one embodiment, said mounting frame (140) has a first and a second lateral side (141, 142) located opposite each other, wherein one of said lateral sides is preferably formed by a transparent planar substrate configured to act as a counter surface (321) against which said tube may be pressed, wherein said mounting frame is configured such that the other of said lateral sides of said mounting frame allows exposure of a central portion (115) of said tube to a temperature controlling device by allowing physical contact of said temperature controlling device to said central portion of said tube through said other of said oppositely located lateral sides and by allowing exertion of pressure by said temperature controlling device to said central portion of said tube through said other of said oppositely located lateral sides, preferably against said counter surface of said transparent planar substrate.

In one embodiment, said mounting frame (140) is further configured to allow analysis of a central portion (115) of said tube by optical detection means, preferably through one of said lateral sides of said mounting frame, more preferably through said lateral side formed by said transparent planar substrate as defined above.

In one embodiment, said central portion (115) of said tube is a portion that has been closed and sealed by said means (130) to reversibly close and seal said deformable transparent tube.

In one embodiment, said mounting frame has a longitudinal axis (143) that is aligned with a longitudinal axis (116) of said tube, and wherein said mounting frame comprises two oppositely located longitudinal ends (144, 145), each of such oppositely located longitudinal ends having an orifice (146, 147), respectively, that is in fluid connection with said oppositely located ends (111, 112) of said tube serving as inlet and outlet of said tube, respectively, wherein each of said orifices is sealable, and preferably comprises means (148, 148') to reversibly close and seal such orifice, such as a cap, a tap, a plug, a stopper, or a screw cap.

In one embodiment, said tube (110) is mounted in said mounting frame (140) such that said oppositely located open ends of said tube are attached to or contact said oppositely located longitudinal ends of said mounting frame, and wherein said mounting frame encompasses a space (149) through which said tube extends, such space being configured to allow exposure or contact of a central portion (115) of said tube to a temperature controlling device and/or to allow analysis of a central portion of said tube by optical detection means.

In one embodiment, said wall (114, 114', 114"), preferably said single wall (114'''), of said tube has a thickness in a range of from 1 μm to 1000 μm, preferably 20 μm to 200 μm, more preferably 50 μm to 150 μm, and/or wherein the diameter of said interior space, when having a circular or oval cross-section, is in the range of from 0.1 cm to 5 cm, and/or wherein a height of said interior space of said tube, when having a flat, noncircular cross-section, is in a range of from 5 μm to 500 μm, preferably 5 μm to 200 μm, more preferably 10 μm to 150 μm.

In one embodiment, said tube is a seamless tube and preferably does not have any edges, in particular no perimeter edges e.g. as would arise from a sealing process. This has the advantage that gas will not be trapped at any such edges. In one embodiment, said tube does not have nucleic acids attached to the inside of said one or several walls lining the interior space of said tube.

In one embodiment, said tube is not a branched tube or a tube with one or several bends or constrictions in it. In one embodiment, said tube does not comprise a plurality of chambers or reservoirs or compartments or interior spaces.

In one embodiment, said tube is a tube having a single interior space and has a longitudinal axis, wherein said oppositely located open ends of said tube are arranged such that they are aligned with each other and along said longitudinal axis.

In one embodiment, said oppositely located open ends are of the same size, wherein preferably they have openings of substantially the same diameter or of a diameter that differs by no more than 10%.

In one embodiment, said deformable transparent tube is made of a material which is transparent in or within a range of from 250 nm to 950 nm, preferably transparent in a range of from 400 nm to 600 nm, and/or in a range of from 450 nm to 650 nm, and/or in a range of from 500 nm to 700 nm, and/or in a range of from 550 nm to 750 nm, and/or in a range of from 600 nm to 800 nm, and which allows an analysis of any content, if present, within said interior space of said tube by means of optical spectroscopy and/or imaging, wherein, preferably, said material is selected from styrene-butadiene-rubber, silicone-rubber, polyvinyl butyral, polyurethane, polyisobutylene, polyhydroxybutyrate, polyhydroxyalkanoate, polyether-block-amide, rubber, gummi arabicum, isoprene-rubber, fluoro-rubber, ethylene-vinylacetate-copolymer, ethylene-propylenediene-rubber copolymer, ethylene-ethylacrylate-copolymer, chloroprene-rubber, ethyl-rubber, butadiene-rubber, acrylonitrile-methylmethacrylate-copolymer, acrylonitrile-chlorinate-polyethylene-styrene-copolymer, acrylonitrile-butadiene-acrylate-copolymer, polyester (PES), polyethylene terephthalate (PET), polyethylene (PE), high-density polyethylene (HDPE), polyvinyl chloride (PVC), polyvinylidene chloride (PVDC), low-density polyethylene (LDPE), polypropylene (PP), polystyrene (PS), high impact polystyrene (HIPS), polyamides (PA), acrylonitrile butadiene styrene (ABS), polyethylene/acrylonitrile butadiene styrene (PE/ABS), polycarbonate (PC), polycarbonate/acrylonitrile butadiene styrene (PC/ABS), polyurethane (PU), and combination of any the foregoing or its copolymers.

In a further aspect, the present invention also relates to the use of a sample cartridge according to the present invention for generating and/or processing a dispersion of particles, cells or droplets, in particular a suspension of particles or cells, or an emulsion of droplets.

In one embodiment, said processing is one or several of the following activities: incubating said dispersion of particles, cells or droplets, performing a biochemical reaction with said dispersion of particles, cells or droplets, binding one or several analytes to said particles, cells or droplets and thereafter removing any unbound analytes and other unbound material from said particles, cells or droplets, exchanging a liquid phase of said dispersion, analysing said dispersion of particles, cells or droplets.

In one embodiment, said use comprises
  filling a dispersion of particles, cells or droplets, in particular a suspension of particles or cells, and, optionally, one or several additional reagents into said tube;
  optionally, arranging said particles, cells or droplets in a monolayer;
  performing a biochemical reaction within said tube and/or incubating said tube at one or several defined reaction conditions, in particular one or several temperature conditions;
  analyzing the results of such biochemical reaction and/or of such incubation.

In one embodiment, said biochemical reaction is not a sequencing process and/or does not involve the use of any nucleic acids attached to the inside of said one or several walls lining the interior space of said tube.

In one embodiment, said use comprises:
  Filling a dispersion of particles, cells or droplets, into said tube, said dispersion comprising a first liquid, preferably a first aqueous liquid;
  removing said first liquid from said particles, cells or droplets in said tube, e.g. by allowing said first liquid to pass said means to withhold, e.g. by centrifugation, gravitational force or by suction, whilst said particles, cells or droplets are withheld by said means to withhold;
  adding a second liquid, preferably a second aqueous liquid, containing an analyte to said tube;
  incubating said particles, cells or droplets in said second liquid to allow or facilitate binding of said analyte to said particles, cells or droplets;
  removing said second liquid from said particles, cells or droplets in said tube, e.g. by allowing said second liquid to pass said means to withhold, e.g. by centrifugation, gravitational force or by suction, whilst said particles, cells or droplets are withheld by said means to withhold; optionally washing said particles, cells or droplets in order to remove any unbound analytes and unbound material from said particles, cells or droplets;
  resuspending particles in a third liquid, preferably a non-aqueous liquid, by adding such third liquid to said tube;
  optionally, arranging said particles, cells or droplets in a monolayer;
  performing a biochemical reaction within said tube and/or incubating said tube at one or several defined reaction conditions, in particular one or several temperature conditions;
  analyzing the results of such biochemical reaction and/or of such incubation.

In one embodiment, said biochemical reaction is not a sequencing process and/or does not involve the use of any nucleic acids attached to the inside of said one or several walls lining the interior space of said tube.

In a further aspect, the present invention also relates to a method of generating a dispersion of droplets, in particular an emulsion of droplets, said method comprising the steps: providing a cartridge according to the present invention as defined above, mixing, within the tube of said cartridge, an aqueous phase and an oily liquid phase, thus generating a dispersion, in particular an emulsion of droplets.

In yet a further aspect, the present invention also relates to a method of generating a dispersion of solid or semi-solid, e.g. gel, particles, said method comprising the steps: providing a cartridge according to the present invention as defined above, mixing, within the tube of said cartridge, an aqueous phase and an oily liquid phase, thus generating a dispersion, in particular an emulsion of droplets, wherein one of said phases additionally contains either solid particles or one or several components capable of forming a gel or a solid upon changing at least one environmental condition around said component, wherein, if one of said phases additionally contains one or several components capable of forming a gel or solid, said method additionally comprise the step. inducing the formation of a gel or of a solid by changing said at least one environmental condition around said component, thereby converting said droplets into particles and generating a dispersion of particles within said tube.

In one embodiment, said at least one environmental condition is selected from temperature, pH, pressure, light of a defined wavelength range, ultrasound, and presence of polymerization inducing chemical(s).

In yet a further aspect, the present invention also relates to a device (300) for incubating a dispersion of particles, cells or droplets, in particular a suspension of particles or cells, or an emulsion of droplets, and/or for performing a biochemical reaction therewith, said device comprising:
  a sample cartridge (100) according to the present invention, as defined above;
  a temperature controlling unit (310) having a temperature controlling surface (311) and being adapted to heat and/or cool via said temperature controlling surface;
  wherein the device is configured such that said tube of said sample cartridge, in particular a central portion (115) of said tube, can be brought or is in contact with said temperature controlling surface (311) by way of one of said lateral sides (141, 142) and can be or is pressed by or against said temperature controlling surface (311), whereby said tube, when pressed by or against said temperature controlling surface, is deformed and wherein said interior space (113) of said pressed tube has a flat, non-circular cross-section.

In one embodiment, the device further comprises
  a counter unit (320) located opposite said temperature controlling unit (310) at a distance therefrom and having a counter surface (321) facing said temperature controlling surface (311), wherein said counter unit either is said transparent planar substrate, if present in said cartridge, forming one of said lateral sides (141, 142) of said cartridge and configured to act as a counter surface (321) against which said tube may be pressed, or said counter unit (320) is a separate component not forming part of the cartridge and being provided in said device (300) separate from said cartridge, said separate component being preferably configured to be operable so as to exert pressure via said counter surface (321) on said tube that is in contact with said temperature controlling surface (311) or being operable to be positioned at a defined distance to said sample cartridge (109).

In one embodiment, either the temperature controlling surface or the counter surface is transparent or both, preferably in a range of from 250 nm to 950 nm, preferably transparent in a range of from 400 nm to 600 nm, and/or in a range of from 450 nm to 650 nm, and/or in a range of from 500 nm to 700 nm, and/or in a range of from 550 nm to 750 nm, and/or in a range of from 600 nm to 800 nm.

In one embodiment, the temperature controlling unit has a receiving portion (312) for receiving said tube wherein said receiving portion allows for the fixation of said tube on said temperature controlling surface (311).

In one embodiment, said device further comprises:
one or several spacers (330, 330') being located on said counter unit (320), preferably said counter surface (321), or on said temperature controlling unit (310), preferably said temperature controlling surface (311), said spacer (330, 330') having a height represented by the following formula:

$$H_S = 2 \times T + H_{CS},$$

wherein $H_S$=height of spacer; T=wall thickness of deformable transparent tube, $H_{CS}$=height of interior space of tube when having a flat, non-circular cross-section, wherein, if there are several spacers (330, 330'), the height of each spacer is the same $H_S$, wherein preferably $H_S$ is in a range of from 7 μm to 2500 μm.

In one embodiment, the device further comprises optical detection means (340), said optical detection means being configured to be capable of detecting and/or analyzing the content of said interior space (113) of said tube by means of optical spectroscopy and/or imaging, wherein preferably such detection and/or analysis is performed with a beam path going through a central portion (115) of said tube, and either said temperature controlling surface (311) or said counter surface (321) or both.

In one embodiment, said device comprises a plurality of sample cartridges (100, 100', 100"), as defined above.

In yet a further aspect, the present invention also relates to the use of the device according to the present invention for generating and/or processing a dispersion of particles, cells or droplets, in particular a suspension of particles or cells, or an emulsion of droplets, wherein said use involves a sample cartridge according to the present invention as defined above and is performed as defined above.

The inventors have surprisingly found that the use of an open ended deformable transparent tube comprised within a cartridge allows to achieve the desired outcome. The tube is adapted to receive a dispersion of particles, cells or droplets in an interior space of the tube formed by one, two or several walls of the tube, and the tube is configured such that the interior space of the tube, when having received the suspension or emulsion or dispersion, has a circular or oval cross-section, and the interior space of the tube has a flat, non-circular cross-section when the tube is pressed against a surface. The sample cartridge in accordance with the present invention furthermore comprises means to withhold the particles, cells or droplets in the deformable transparent tube, whilst such means allow the free passage or transfer of liquid through it. The means to withhold the particles are typically located at one or both ends of the tube. Preferably, such means is/are a filter, a membrane, a grid, a mesh, a sieve or other structure allowing the passage of liquid through it whilst retaining said particles. The tube is deformable to the extent that when it is being filled and after it has been filled with liquid, such as with a dispersion of particles, cells or droplets, it has a circular or oval cross-section, and when the tube has received said liquid and is pressed in such filled state against a surface it has a flat, non-circular cross-section. This allows for the reaction space that is available to have one dimension sufficiently small to enable a rapid heat transfer from a temperature controlling surface, if the tube is pressed against such surface. By appropriately choosing and defining the way the tube is pressed against a surface, an optimized reaction space can be generated. For example, if the tube is pressed against a surface only at one part, e. g. at one end, the interior space of the tube may adopt a wedge shape which allows the directing and removal of any gas/air that may have become trapped during the filling process of the tube. This venting process can be supported by gravity. When the tube is subsequently pressed against a surface over substantial parts of the tube, for example, over a substantial central portion thereof, the tube will then adopt the aforementioned flat, non-circular-cross section along the entire length of such central portion. The interior space of said pressed tube may then have a height which is just sufficiently large enough to accommodate a single layer (monolayer) of particles, cells or droplets. Hence, in such embodiment of the sample cartridge and the method according to the present invention, the particles, cells or droplets are arranged in a monolayer. This is particularly advantageous, given that such arrangement then allows both fast and efficient heat transfer and the analysis of individual particles, cells or droplets without any overlap with other particles. In one embodiment, the provision of a suitable height of the interior space depends on various factors, including the pressure exerted on the tube, the size of the particles, the elasticity, if any, of the tube, the height of the spacers provided, if any, and others. Hence, in one embodiment, the cartridge according to the present invention may be used for arranging a sample containing a dispersion of particles, such that the particles form a monolayer. In a preferred embodiment, the deformable transparent tube has a single wall, and the interior space is lined by the single wall. This has the advantage that gas formation at edges, e. g. between different parts of the tube is reduced, because there are no edges. In one embodiment, said tube is a seamless tube and preferably does not have any edges, in particular no perimeter edges e.g. as would arise from a sealing process. This has the advantage that gas will not be trapped at any such edges. In one embodiment, said tube does not have nucleic acids attached to the inside of said one or several walls lining the interior space of said tube. In one embodiment, said tube is an elastic tube and is made of an elastic material, preferably an elastomeric material. In one embodiment said tube is made of a material the glass transition temperature of which is below the temperature at which said material is used. In another embodiment, said tube is a plastic tube and is made of a plastic material, preferably a thermoplastic material. In one embodiment, said tube is made of a polymeric material, preferably a polymeric material selected from styrene-butadiene-rubber, silicone-rubber, polyvinyl butyral, polyurethane, polyisobutylene, polyhydroxybutyrate, polyhydroxyalkanoate, polyether-block-amide, rubber, gummi arabicum, isoprene-rubber, fluoro-rubber, ethylene-vinylacetate-copolymer, ethylene-propylenediene-rubber copolymer, ethylene-ethylacrylate-copolymer, chloroprene-rubber, ethyl-rubber, butadiene-rubber, acrylonitrile-methylmethacrylate-copolymer, acrylonitrile-chlorinate-polyethylene-styrene-copolymer, acrylonitrile-butadiene-acrylate-copolymer, polyester (PES), polyethylene terephthalate (PET), polyethylene (PE), high-density polyethylene (HDPE), polyvinyl chloride (PVC), polyvinylidene chloride (PVDC), low-density polyethylene (LDPE), polypropylene (PP), polystyrene (PS), high impact polystyrene (HIPS), polyamides (PA), acrylonitrile butadiene styrene (ABS), polyethylene/acrylonitrile butadiene styrene (PE/ABS), polycarbonate (PC), polycarbonate/acrylonitrile butadiene styrene (PC/ABS), polyurethane (PU), and combination of any the foregoing or its copolymers.

In one embodiment, the sample cartridge according to the present invention further comprises means to reversibly close and seal the deformable transparent tube at one or both of said oppositely located ends. Such means to reversibly close and seal the transparent tube at one or both ends may be arranged such that one end is closed and sealed thereby whilst the other end temporarily still stays open such that the volume of the interior space is adapted. Through the remaining open end, excess liquid sample or unwanted gas/air may be removed. In a preferred embodiment, there are means to reversibly close and seal the deformable transparent tube at both oppositely located ends. In such embodiment, the second means may subsequently also be closed allowing the deformable elastic transparent tube to be sealed at both ends and comprising a defined interior space which is an optimized reaction space. Preferably, the means to reversibly close and seal the deformable transparent tube are configured such that they withstand pressure and/or heat, when being closed/sealed. This has the advantage that the sample within the interior space may be exposed to higher temperatures, such as temperatures >80° C., e. g. 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C., which may, for example, be encountered during polymerase chain reaction (PCR) or other processes requiring a temperature cycling, including the attainment of such high temperatures and the sample cartridge may be exposed to external forces, such as during a centrifugation, without the risk of the tube losing sample from the interior space. In some special cases the interior space may be heated up to temperatures >120° C. which may be beneficial for ultra-fast thermocycling of the sample.

In one embodiment, the means to reversibly close and seal is a clamp or a pair of clamps located at one or both of said opposite ends of the tube.

In one embodiment, the sample cartridge according to the present invention further comprises a mounting frame that is connected to and holds said tube at said oppositely located ends of the tube. Such mounting frame is configured to allow the addition of material, e.g. liquid or solid or a mixture thereof, to the interior space of said tube via one of said ends serving as inlet, and/or removal of material, e.g. liquid or solid or a mixture thereof, from said interior space of said tube via the other of said ends serving as outlet.

The means to withhold the particles being located at one or both ends of said tube are either located within the tube, or at the end(s) of said tube within the sample cartridge but outside of said tube.

The mounting frame of the sample cartridge provides stability to the sample cartridge and allows a protection of the tube whilst enabling a controlled and directed access to such tube. In one embodiment, such mounting frame is made of a material that provides for such mechanical stability. A plurality of suitable materials may be envisaged, such as plastics, metal, wood or glass, ceramic. In one embodiment, the mounting frame has a first and a second lateral side located opposite each other, wherein one of said lateral sides is preferably formed by a transparent planar substrate configured to act as a counter surface against which the tube may be pressed. The mounting frame is configured such that the other of the lateral sides of said mounting frame, i. e. the side that is not formed by a transparent planar substrate, remains open and allows exposure of a central portion of said tube to a temperature controlling device which is not a part of the sample cartridge. This lateral side allows physical contact of a temperature controlling device to said central portion of said tube and the exertion of pressure by such temperature controlling device to said central portion of said tube. For example the temperature controlling device may press the tube against the counter surface of said transparent planar substrate. The mounting frame is further configured to allow an analysis of a central portion of the tube by optical detection means (such optical detection means again not forming part of the sample cartridge). Such optical detection/analysis may occur through one of the two lateral sides of said mounting frame, preferably through the lateral side that is formed by the transparent planar substrate, as defined further above.

In one embodiment, the central portion of the tube which is analyzed, is a portion that has been closed and sealed by the means to reversibly close and seal the deformable transparent tube. "Analysis of a central portion of said tube", as used herein, is meant to refer to an analysis of the interior space of said tube within such central portion. Analysis may be done by any suitable means, for example optical detection means or imaging means allowing an optical analysis or imaging. In one embodiment, the mounting frame is configured such that it allows a centrifugation of the sample cartridge. Preferably, it enables such centrifugation by being adapted and shaped to allow the sample cartridge to be inserted and fitted into a centrifuge tube and/or centrifuge rotor. In one embodiment, the sample cartridge is able to withstand centrifugal acceleration of up to 10.000 g. In one embodiment, the sample cartridge is "centrifugable". Such "centrifugablility" is meant to refer to the capability of such sample cartridge being centrifuged without becoming damaged, permanently deformed or otherwise unwanted affected in an unwanted manner. In one embodiment, the sample cartridge is suitable and intended to be centrifuged.

In a preferred embodiment, the mounting frame of the sample cartridge has a longitudinal axis that is aligned with a longitudinal axis of the deformable transparent tube. The mounting frame of the sample cartridge, in such embodiment, comprises two oppositely located longitudinal ends, each of which has an orifice, respectively, and such orifice is in fluid connection with the respective end of the tube next to it, i. e. the end serving as inlet and the end serving as outlet of said tube. In such embodiment, each of these orifices is sealable and, preferably comprises means to reversibly close and seal such orifice. Such means to reversible close and seal such orifice may be any suitable means, for example a cap, a tap, a plug, a stopper, or a screw cap. The advantage of such sealable orifices is, again, that this increases the stability and rigidity of the cartridge and facilitates centrifugation of such cartridge. Furthermore, the means to reversibly close and seal the orifice(s) may be configured such that they themselves are capable to receive a volume of liquid, for example, when the sample cartridge is centrifuged to separate the particles of a dispersion which has been added to the interior space of the tube, from the liquid. For example, such means, e. g. a cap, screwcap, tab, plug or stopper may be provided with an interior void volume capable of receiving such liquid. Upon application of a force, such as a gravitational or centrifugational force to the cartridge, the particles, cells or droplets are retained by the means to withhold in the sample cartridge, whilst the liquid passes through such means and is received by the means to reversibly close and seal the orifice(s) e.g. the cap. Once, received within such means to irreversibly close and seal, the liquid can then be withdrawn and discarded or otherwise handled.

In one embodiment, the deformable transparent tube is mounted in the mounting frame of the cartridge such that the oppositely located open ends of the tube are attached to the oppositely located longitudinal ends of the mounting frame or contact them. In such embodiment, the means to withhold the particles, cells or droplets are either located at one or both ends of the tube, just within the tube, or they are located outside of the tube at the oppositely located longitudinal end(s) of the mounting frame. In one embodiment, the mounting frame encompasses a space through which the tube extends longitudinally, and such space is configured to allow exposure or a contact of a central portion of said tube to a temperature controlling device (not forming part of the sample cartridge), and/or to allow analysis of a central portion of said tube by optical detection means (again, such optical detection means not forming part of the sample cartridge).

In one embodiment, the wall of said tube, preferably the single wall, of said tube has a thickness in a range of from 1 μm to 1000 μm, preferably 20 μm to 200 μm, more preferably 50 μm to 150 μm. In one embodiment, the diameter of the interior space, when having a circular or oval cross-section, is in the range of from 0.1 cm to 5 cm. In one embodiment, when the tube has a flat, non-circular cross-section, a height of the interior space of said tube is in the range of from 5 μm to 500 μm, preferably 5 μm to 200 μm, more preferably 10 μm to 150 μm. In one embodiment, such height of said interior space of said tube is chosen such that it matches the dimensions of the particles, cells or droplets that are part of the sample to be analyzed/processed. In one embodiment, the height of said interior space of said tube when having a flat, non-circular cross-section matches, is the same or is approximately the same as the height of a single particle, cell or droplet forming part of the sample, but it may also be additionally 1-10 μm bigger than the height of a single particle, cell or droplet. The correspondence in size of the height of the interior space with the height of a single particle allows the processing and/or analysis of a monolayer of particles, cells or droplets within the interior space of the tube to be done efficiently. The analysis and/or processing could be done bulk-wise (e.g. taking an analytical image from the tube) or on a single particle level (e.g. manipulate single particle(s) by a laser beam). In one embodiment, the transparent tube is made of a material which is transparent to light in or within a range of from 250 nm to 950 nm. Hence, it can be transparent either over the entire range, or it is transparent within a partial range thereof. Depending on the application of the sample and of the method of analyzing such sample, different ranges of transparency may be suitable. In one embodiment, the material is transparent in a range of from 400 nm to 600 nm, and/or in a range of from 450 nm to 650 nm, and/or in a range of from 500 nm to 700 nm, and/or in a range of from 550 nm to 750 nm, and/or in a range of from 600 nm to 800 nm. At least the material combination has to be transparent in that way that the selected optical detection principle can be performed. That could e. g. lead to situation where in case of fluorescence detection, the material is transparent or semitransparent for just two wavelengths. Furthermore the side of the tube that is not facing optical detection means or an optical detection unit could be treated to change optical properties to improve this optical detection e.g. colored black. In one embodiment, the material of said deformable transparent tube allows an analysis of any content, if present, within said interior space of said tube by means of optical spectroscopy and/or imaging. In one embodiment, the tube is made of a material that is ductile and/or plastic and/or elastic and/or thermoformable and/or thermoplastic-elastomeric or it could have any other flexibility properties to have the ability to form the "detection chamber". This is valid for almost every plastic material at least beyond the glass transition temperature. In one embodiment, the tube is made of a material selected from styrene-butadiene-rubber, silicone-rubber, polyvinyl butyral, polyurethane, polyisobutylene, polyhydroxybutyrate, polyhydroxyalkanoate, polyether-block-amide, rubber, gummi arabicum, isoprene-rubber, fluoro-rubber, ethylene-vinylacetate-copolymer, ethylene-propylenediene-rubber copolymer, ethylene-ethyl-acrylate-copolymer, chloroprene-rubber, ethyl-rubber, butadiene-rubber, acrylonitrile-methylmethacrylate-copolymer, acrylonitrile-chlorinate-polyethylene-styrene-copolymer, acrylonitrile-butadiene-acrylate-copolymer, polyester (PES), polyethylene terephthalate (PET), polyethylene (PE), high-density polyethylene (HDPE), polyvinyl chloride (PVC), polyvinylidene chloride (PVDC), low-density polyethylene (LDPE), polypropylene (PP), polystyrene (PS), high impact polystyrene (HIPS), polyamides (PA), acrylonitrile butadiene styrene (ABS), polyethylene/acrylonitrile butadiene styrene (PE/ABS), polycarbonate (PC), polycarbonate/acrylonitrile butadiene styrene (PC/ABS), polyurethane (PU), and combination of any the foregoing or its copolymers.

The present invention also relates to the use of a sample cartridge as defined above, for generating and/or processing a dispersion of particles, cells or droplets, in particular a suspension of particles or cells, or an emulsion of droplets. Likewise, the present invention also relates to a method of generating and/or processing a dispersion of particles, cells or droplets, in particular a suspension of particles, or cells or an emulsion of droplets, wherein in such method, a sample cartridge, as defined above, is used.

In one embodiment, said processing is one or several of the following activities: incubating said dispersion of particles, cells or droplets, performing a biochemical reaction with said dispersion of particles, cells or droplets, binding one or several analytes to said particles, cells or droplets and thereafter removing any unbound analytes and other unbound material from said particles, cells or droplets, exchanging a liquid phase of said dispersion, and/or analyzing said dispersion of particles, cells or droplets.

In one embodiment, said use comprises:
  Filling a dispersion of particles, cells or droplets, in particular a suspension of particles or cells, and, optionally, one or several additional reagents into said tube;
  performing a biochemical reaction within said tube and/or incubating said tube at one or several defined reaction conditions, in particular one or several temperature conditions;
  analyzing the results of such biochemical reaction and/or of such incubation.

In one embodiment, the use preferably comprises
  filling a dispersion of particles, cells or droplets, into said tube, said dispersion comprising a first liquid, preferably a first aqueous liquid;
  removing said first liquid from said particles, cells or droplets in said tube, e. g. by allowing said first liquid to pass said means to withhold, e. g. by centrifugation, gravitational force or by suction, whilst said particles, cells or droplets are withheld by said means to withhold;

adding a second liquid, preferably a second aqueous liquid, containing an analyte to said tube;

incubating said particles, cells or droplets in said second liquid to allow or facilitate binding of said analyte to said particles, cells or droplets;

removing said second liquid from said particles, cells or droplets in said tube, e. g. by allowing said second liquid to pass said means to withhold, e. g. by centrifugation, gravitational force or by suction, whilst said particles, cells or droplets are withheld by said means to withhold; optionally washing said particles, cells or droplets in order to remove any unbound analytes and unbound material from said particles, cells or droplets;

re-suspending said particles in a third liquid, preferably a non-aqueous liquid, by adding such third liquid to said tube;

performing a biochemical reaction within said tube and/or incubating said tube at one or several defined reaction conditions, in particular one or several temperature conditions;

analyzing the results of such biochemical reaction and/or of such incubation.

With respect to the dispersion of particles, cells or droplets and the particles, cells or droplets, any suitable particles, cells or droplets may be used in conjunction with the sample cartridges according to the present invention provided they allow the desired processing/reaction to be performed. Such particles may be micro beads which may have capture molecules attached. Such particles are, in principle, known. Suitable examples are for example disclosed in Microfluidic Methods for Molecular Biology, Lu & Verbridge Editors, Springer International Publishing Switzerland 2016. Further suitable examples, are for example, disclosed in co-pending European Patent Application No. 16 207 455.3 filed on Dec. 30, 2016. These particles are examples of prefabricated micro particles for performing a digital detection of any analyte in a sample having a surface and including a void volume for receiving an aqueous solution and being dispersible in a non-aqueous medium.

In a further aspect, the sample cartridge according to the present invention can be also used to generate an emulsion of droplets or a dispersion of particles. Thus in one embodiment the present invention also relates to the use of a sample cartridge as defined above for generating an emulsion of droplets or a dispersion of particles. It also relates to a method of generating an emulsion of droplets or a dispersion of particles wherein a sample cartridge as defined above is used. Such generating may be done as a standalone process or prior to any incubation and other processes such as processes relating to a detection or analysis of reaction products. Hence, when it is described further above that a dispersion of particles, cells or droplets is filled into said tube (of the cartridge), this is also meant to include the possibility of a generation (ab initio) of a dispersion of particles, cells or droplets, such as an emulsion of droplets or a dispersion of particles within said tube. In one embodiment, the sample cartridge according to the present invention can be used to generate aqueous droplets, i.e. a water-in-oil-emulsion. In another embodiment, the sample cartridge according to the present invention can be used to generate oily droplets, i.e. an oil-in-water-emulsion. In order to generate a stable emulsion, emulsifiers may be used. Such emulsifiers belong to the material category of surfactants with a suitable hydrophilic-lipophilic-balance (HLB) value to create either a water-in-oil (W/O) or oil-in-water (O/W) emulsion. Emulsifiers can be generally classified by the nature of their hydrophilic head and are grouped in anionic, cationic, zwitterionic and nonionic surfactants. Typically the phase with better solubility for the emulsifier is used as the mobile phase.

In one embodiment, for aqueous droplet generation (water-in-oil-emulsion) the tube of the sample cartridge is clamped at one end and filled through the opposing open end with a defined volume of the oil phase liquid which serves as the mobile phase such as commercially available mineral oil(s), paraffin oil(s) or technical fluid(s) (e.g. fluorocarbon based or hydrofluoroether) or suitable organic solvent(s) optionally containing suitable emulsifier(s). Thereafter a defined volume of an aqueous solution which represents in this embodiment the dispersed phase containing materials/solutes that are intended to be enclosed in droplets is added to the tube. In one embodiment, the ratio of the defined volume of oil phase liquid to the defined volume of aqueous solution is in a range of from 1.2:1 to 100:1, preferably from 2:1 to 10:1. The ratio of the mobile phase vs the emulsion phase can vary and depends on the employed materials for the mobile phase, the dispersed phase and the surfactants used to stabilize the emulsion. Multiple protocols can be found in textbooks such as Tadros, Tharwat F., Emulsions, Formation, Stability, Industrial Applications, ISBN 978-3-11-045224-2. Materials that may be contained within the aqueous solution may be amplification reagents, such as PCR Reagents, and may furthermore include amplification targets, detection agents, emulsifiers etc. Typical protocols for emulsion PCR are known, and an Example is described in Williams et al., Nature Methods 3(7):545-550, 2006. After closing the inlet of the cartridge the droplets are generated by agitating the tubing which can be done directly by any suitable means, such as repeatedly compressing the tubing or by other means such as stirring, shaking or by applying ultra sound. After completion of the droplet generation procedure the cartridge may be processed as previously described. For example the droplets may be washed, incubated or exposed to defined reaction conditions, such as one or several temperature conditions, or a biochemical reaction may be performed within said tube.

Additionally, in one embodiment, the droplet forming solution, in this case the aqueous solution, may contain reagents allowing the transformation of droplets into particles or capsules. In such an embodiment, the generated droplets can be further transformed into (solid or semisolid, e.g. gel) particles, e.g. by a gelation process or by a polymerization process. Thus, in this embodiment, the emulsion of generated droplets is subsequently further converted into a suspension of particles. For example, the droplet forming solution, i.e. the aqueous solution, may include a gelling substance, such as agarose or gelatin that may be induced to gel, or it may include suitable monomers or prepolymers that can be induced to polymerize, such as bisacrylamide and a suitable diamine together with a catalyst such as ammonium persulfate in order to initiate an oxido-reduction reaction. Capsules and particles can be formed by well-established means, such as ionotropic gelation, coacervation, interfacial polycondensation, interfacial cross-linking, in-situ polymerization and matrix polymerization. Moreover layer-by-layer techniques may be used in order to build customized capsule arrangements with tailored properties (as outlined in: layer-by-layer assembly of microcapsules and their biomedical applications; Tong W, Song X, Gao C.; Chem Soc Rev. 2012 Sep. 21; 41(18):6103-24).

In such an embodiment, after droplet generation, the cartridge, including the tube and its content, i.e. also the generated droplets, are exposed to gel-inducing or polymerization inducing conditions. In a simple form, such gel-inducing or polymerization inducing conditions may be a change of temperature or an exposure to electromagnetic radiation of a defined wavelength range, such as e.g. UV light. The particles thus generated may be further processed as previously described. For example the particles may be washed, incubated or exposed to defined reaction conditions, such as one or several temperature conditions, or a biochemical reaction may be performed within said tube.

By applying different ratios of reagents oil in-water-emulsions with the aqueous phase serving as the continuous phase and the oily phase being the dispersed phase may be formed. Suitable protocols may be found in, among others, Tadros, Tharwat F., Emulsions, Formation, Stability, Industrial Applications, ISBN 978-3-11-045224-2.

In a further aspect, the present invention also relates to a device for incubating a dispersion of particles, cells or droplets, in particular a suspension of particles or cells, or an emulsion of droplets, and/or for performing a biochemical reaction therewith, said device comprising:

a sample cartridge as defined above;
a temperature controlling unit having a temperature controlling surface and being adapted to heat or cool via said temperature controlling surface;

wherein the device is configured such that said tube of said sample cartridge, in particular a central portion of said tube, can be brought or is in contact with said temperature controlling surface of said device and can be or is pressed by or against said temperature controlling surface, whereby said tube, when pressed by or against said temperature controlling surface, is deformed, and wherein said interior space of said pressed tube has a flat, non-circular cross-section.

In a preferred embodiment of the device, such device further comprises a counter unit located opposite said temperature controlling unit and having a counter surface facing said temperature controlling surface, wherein said counter unit either is said transparent planar substrate, if present in said cartridge, forming one of said lateral sides of said cartridge and configured to act as a counter surface against which said tube may be pressed, or said counter unit is a separate component not forming part of the cartridge and being provided in said device separate from said cartridge. In one embodiment, this separate component is preferably configured to be operable so as to exert pressure via said counter surface on said tube which is in contact with said temperature controlling surface, or the separate component is operable to be positioned at a defined distance to said sample cartridge. Such defined distance may be in a range of from 0 µm to 10 mm. In case that the counter unit, as a separate component not forming part of the cartridge is positioned at a distance of 0 µm, it effectively contacts the cartridge and may, directly or indirectly exert pressure on the tube of said cartridge. For example, if the cartridge does not have a transparent planar substrate on one of the lateral sides of the mounting frame, the counter unit may contact the tube directly and together with the temperature controlling surface (which presses from the other side) may exert pressure on said tube. Alternatively, if a transparent planar substrate is present in said sample cartridge, the counter unit as a separate component may contact such transparent planar substrate against which said tube may be pressed. Yet, alternatively, the counter unit may also be positioned at a distance from the sample cartridge and or from the transparent planar substrate, if present in said cartridge, and the tube is pressed against the planar surface by the temperature controlling unit/surface.

In one embodiment of the device according to the present invention, the temperature controlling surface or the counter surface is transparent or both, preferably in a range of from 250 nm to 950 nm or in a partial range thereof. In one embodiment, the temperature controlling surface or the counter surface is transparent or both in a range of from 400 nm to 600 nm, and/or in a range of from 450 nm to 650 nm, and/or in a range of from 500 nm to 700 nm, and/or in a range of from 550 nm to 750 nm, and/or in a range of from 600 nm to 800 nm. In one embodiment, the temperature controlling unit of said device has a receiving portion for receiving said tube, wherein said receiving portion allows for the fixation of said tube on said temperature controlling surface. In a preferred embodiment, the device according to the present invention further comprises:

one or several spacers being located on said counter unit, preferably said counter surface, or on said temperature controlling unit, preferably said temperature controlling surface, or on both said counter unit and on said temperature controlling unit, wherein preferably, said spacer has a height represented by the following formula $$H_S = 2 \times T + H_{CS},$$

wherein $H_S$=height of spacer; T=wall thickness of deformable transparent tube, $H_{CS}$=height of interior space of tube when having a flat, non-circular cross-section, wherein, if there are several spacers, the height of each spacer is the same $H_S$, wherein, preferably, $H_S$ is in a range of from 7 µm to 2500 µm, preferably 10 µm to 1000 µm, more preferably 50 µm to 500 µm, more preferably 100 µm to 300 µm. For example if monodisperse suspension of particles with an average diameter of 50 µm and a tubing with a wall thickness of 70 µm is used then a spacer height of approximately 190 µm is appropriate.

Alternately $H_{cs}$ could be adjusted by using an active, movable spacer. By measuring $H_{cs}$, $H_s$ may be controlled precisely. This could be advantageous, in a scenario, where the tube does not have acceptable precision in its wall thickness, e. g. when batches of tube are used that have been produced lacking acceptable or desireable wall thickness tolerances. For the determination of $H_{cs}$ an optical readout system could be used (e.g. optical focus) as well as all other methods are useable (interferometer, TOF, electrical capacity and so on).

In one embodiment, the device according to the present invention further comprises optical detection means, said optical detection means being configured to be capable of detecting and/or analyzing the content of said interior space of said tube by means of optical spectroscopy and/or imaging. Preferably, such detection and/or analysis is performed with a beam path going through a central portion of said tube and through either said temperature controlling surface or said counter surface or both. As pointed out above, in on embodiment, the optical detection means may also be used to determine $H_{cs}$ and may be configured to do so.

In one embodiment, the optical detection means may be integrated in the counter unit or in the temperature controlling unit or in both, or it may be provided separately therefrom.

In one embodiment, the device according to the present invention is configured such that it is able to hold a plurality of sample cartridges according to the present invention. In one embodiment, the device does comprise a plurality of sample cartridges according to the present invention.

The invention is now further described by reference to the figures wherein

Figure 1:
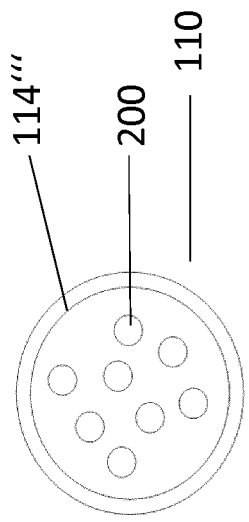
FIG. 1 shows the cross-section of a deformable transparent tube of a sample cartridge according to the present invention containing a dispersion of particles, cells or droplets. It can be seen that the cross-section is circular, and the tube is not pressed or contacted by any surface.
Figure 2:
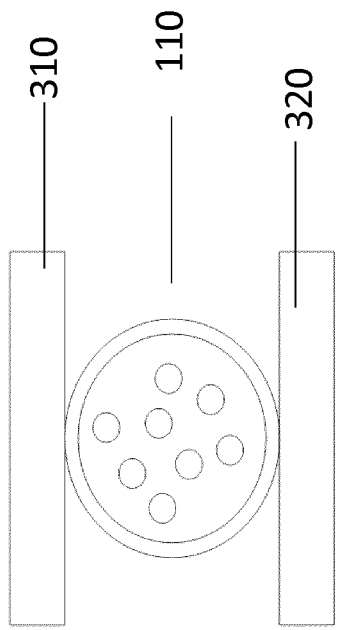
FIG. 2 shows such tube being in contact with a temperature controlling unit and a counter unit, prior to being pressed.
Figure 3:
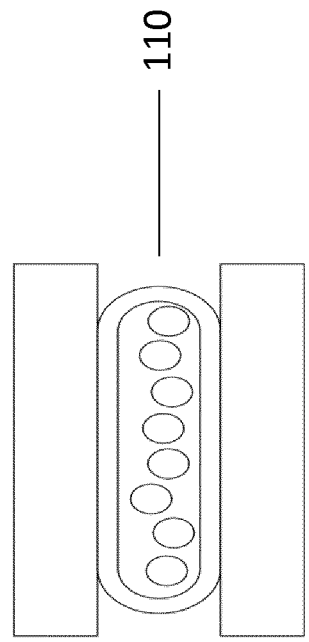
FIG. 3 shows the same tube being pressed between the temperature controlling unit and the counter unit.
Figure 4:
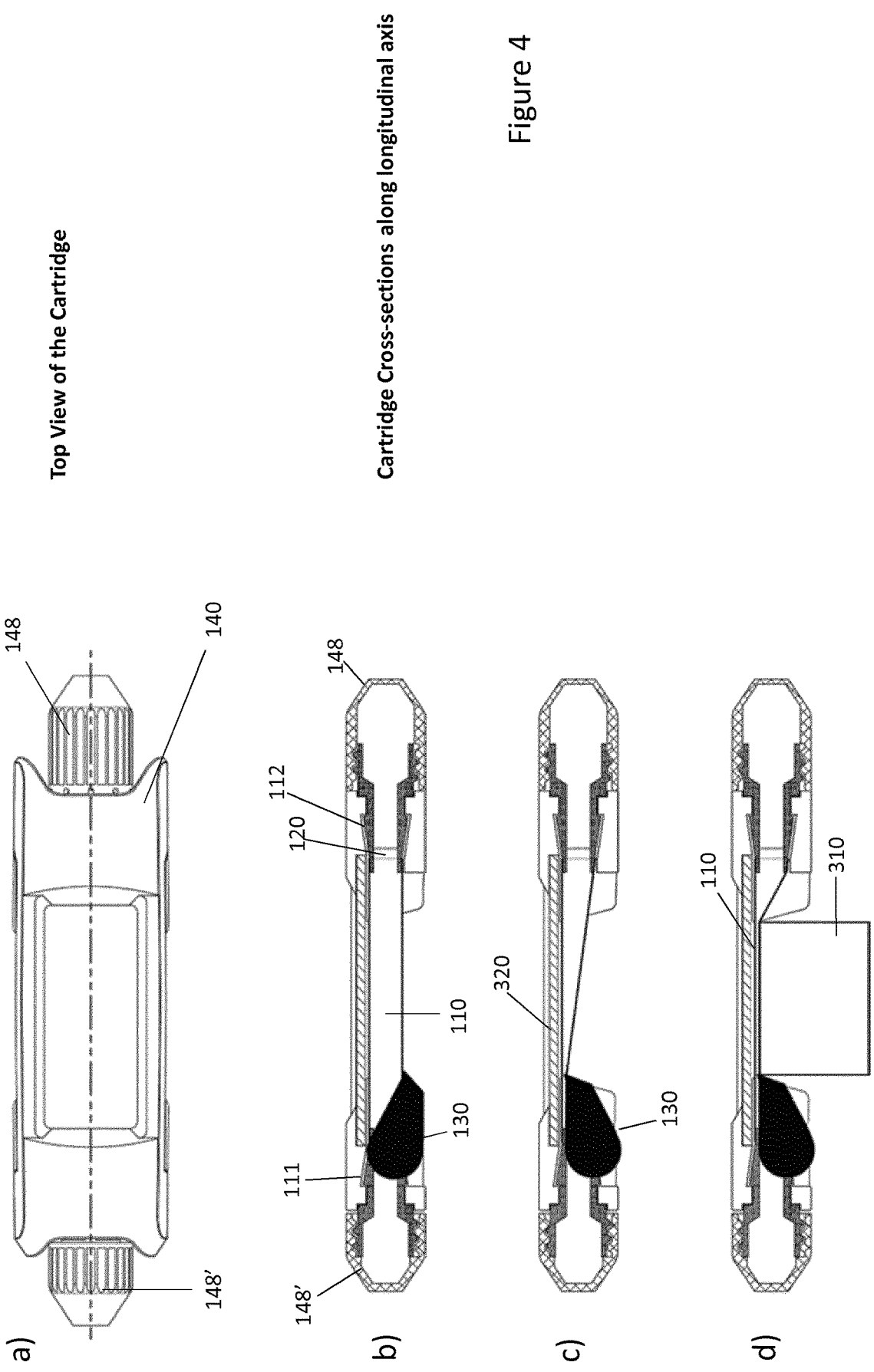

FIG. 4 shows an embodiment of a sample cartridge in accordance with the present invention. On the top panel (a), there is a top view of an embodiment of the sample cartridge showing a mounting frame with two oppositely located longitudinal ends, each of which has an orifice that is closed by a screw cap. Also shown is one of the lateral sides formed by a transparent planar substrate configured to act as a counter surface against which the tube may be pressed. The tube, although theoretically visible through said transparent planar substrate, is not shown. Panels b)-d) show a cross section along the longitudinal axis of panel a), additionally showing means to reversibly close and seal the deformable elastic transparent tube, here in the form of a clamp, located at one end of the transparent tube as well as the tube itself and the means to withhold the particles in the tube (shown as two broken lines towards the right side of the cartridge in the interior). In panel b), the means to reversibly close and seal is open, and in panels c)-d), it is closed, thus closing and sealing one end of the tube, as a result of which, in panel c) the tube and its interior space adopts a wedge shape. In panel d), a temperature controlling device, having a temperature controlling surface is being pressed against the tube, thus pressing the tube against the counter surface formed by the transparent planar substrate of the sample cartridge. Depending on the pressure exerted and the dimensions of the tube, the interior space of the tube may have a height that is just enough to accommodate a monolayer of particles, cells or droplets. This allows an analysis of individual particles without overlap. Also shown in panels b)-d) in cross-section are both lateral sides of the mounting frame, located opposite each other, one of such lateral sides being formed by a transparent planar substrate, configured to act as a counter surface against which the tube may be pressed, and the other of such lateral sides of the mounting frame allowing exposure of a central portion of the tube to a temperature controlling device by allowing physical contact of said temperature controlling device to the central portion of said tube through such other, oppositely located lateral side and by allowing exertion of pressure by said temperature controlling device to such central portion of the tube.

FIG. 5 shows an embodiment of a sample cartridge in accordance with the present invention which is contacted on one of the two lateral sides by a temperature controlling device, and wherein on the other lateral side of said cartridge, there is optical detection means that are located in, form part of or, simply, are a counter unit located opposite the temperature controlling unit. On the left side (panel a)), there is a cross-section, on the right side (panel b)), there is a full view of the arrangement of the sample cartridge within the device for incubating a dispersion of particles, cells or droplets. The particles or the cells or droplets are spread across the flat tube, preferably as a monolayer; the tube is pressed against the counter surface of the counter unit by a/the temperature controlling unit.

Figure 6:
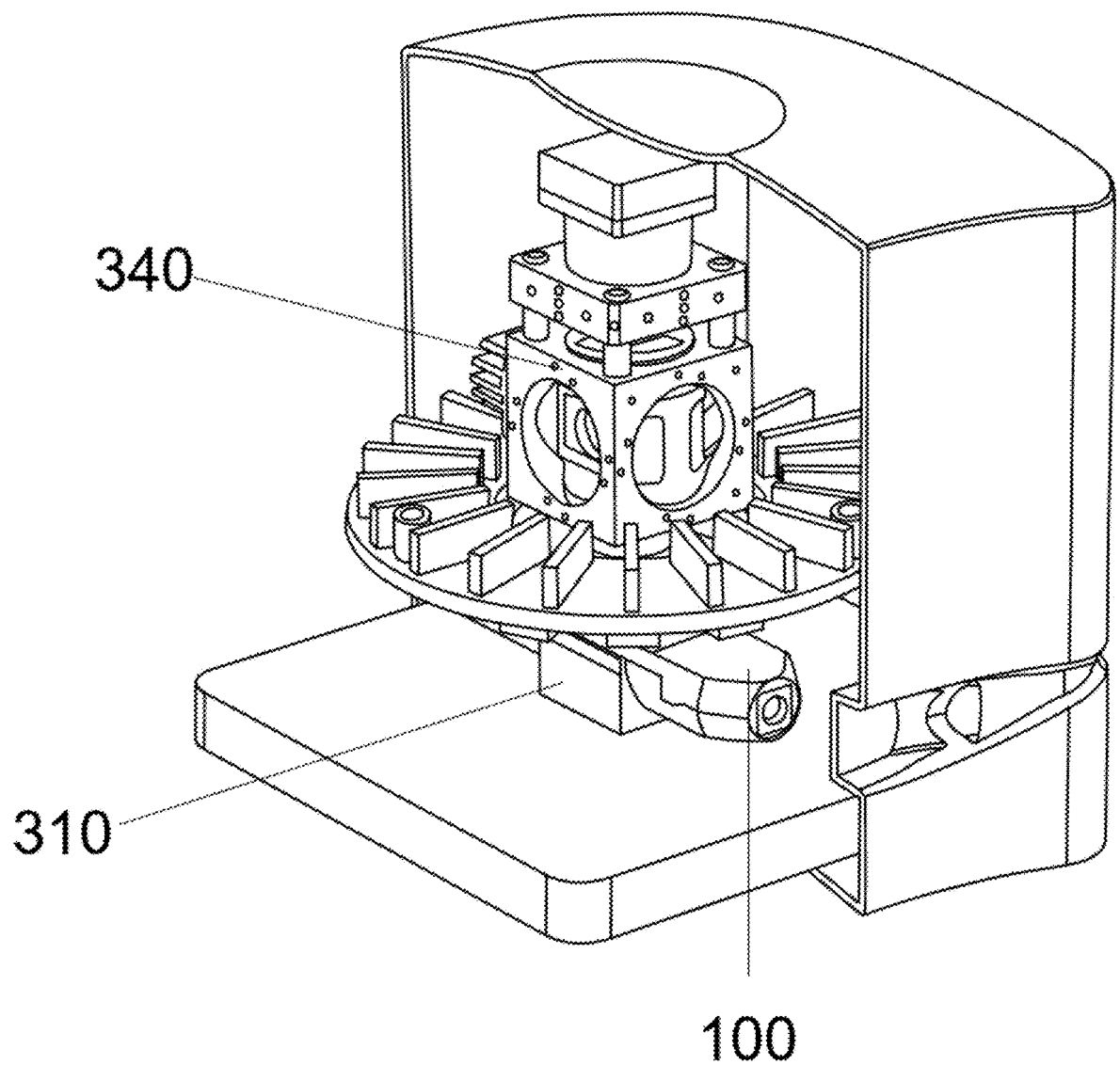

FIG. 6 shows an embodiment of a device for incubating a dispersion of particles, cells or droplets in accordance with the present invention. The device is shown having a housing into which a sample cartridge as defined-above, has been inserted and against which, from one of the lateral sides of the mounting frame, a temperature controlling unit is pressed. Furthermore, shown are the optical detection means which are located on the other side of the cartridge.

Figure 7:
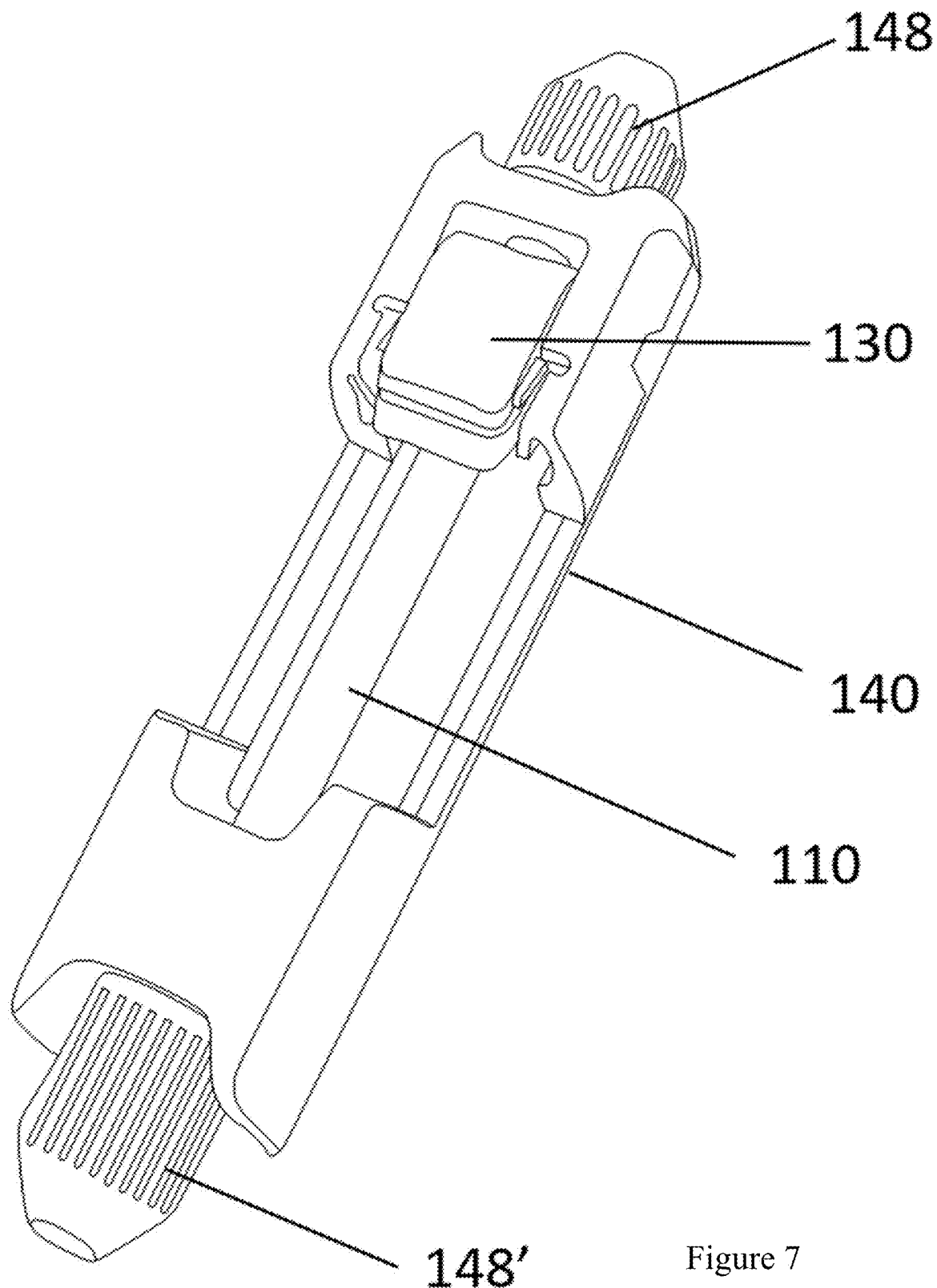

FIG. 7 shows an embodiment of an example cartridge in accordance with the present invention, including a mounting frame, a deformable transparent tube with two oppositely located open ends serving as inlet and outlet, means to reversibly close and seal the tube at one end, in the form of a clamp, and furthermore, means to reversibly close and seal the orifices of the mounting frame, in the form of two screw caps. In this example, one or both of the screw caps are endowed with an interior void volume allowing to receive and hold a liquid which has passed through the means to withhold the particles within the cube.

FIG. 8 shows an embodiment of an example cartridge with a clamp in open position and the tube having a circular cross-section (left side). Once the clamp has been moved into a closed position, the tube has a circular cross-section at one end and a flat, non-circular cross-section at the other end, thus adopting a wedge-shape (right side).

Figure 9:
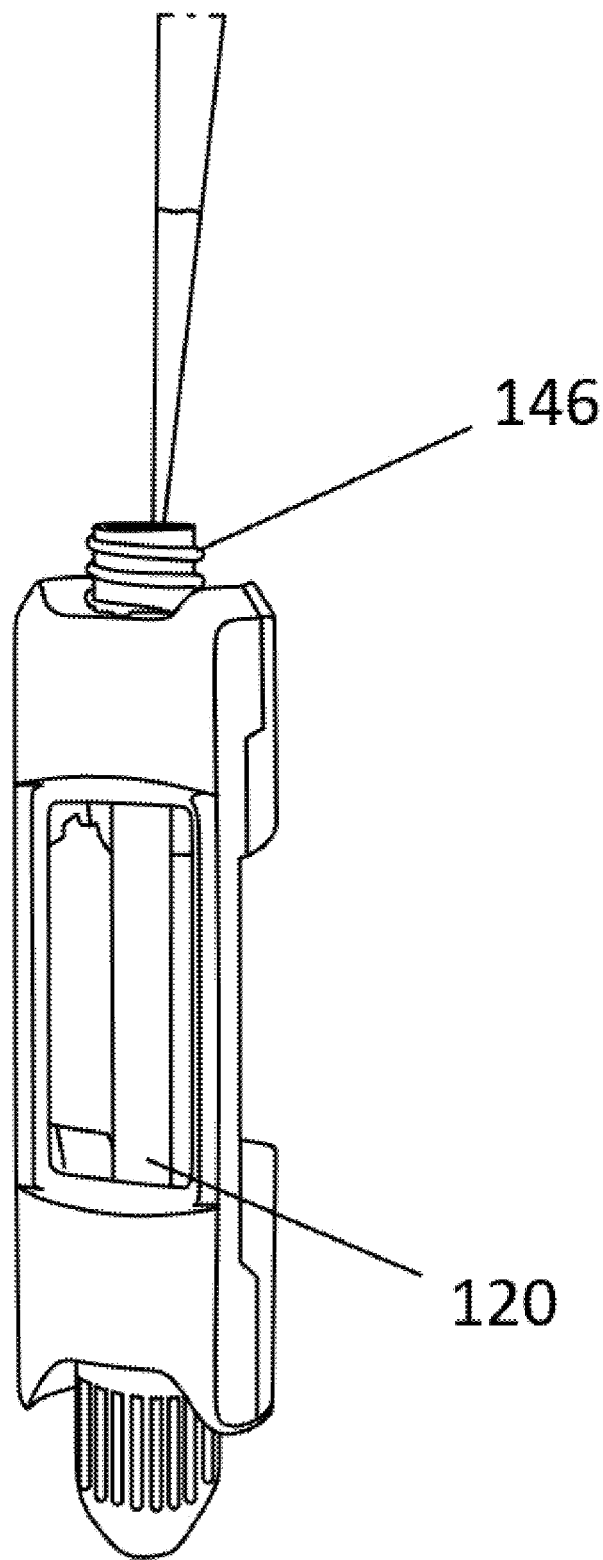

FIG. 9 shows an embodiment of a sample cartridge wherein the top screw cap has been removed, whilst the lower screw cap remains on the lower orifice. A pipette tip, including liquid to be applied to the sample cartridge is shown at the top, such liquid also containing particles. A sample is thus applied to the cartridge to the open top orifice. The dispersion passes through the tube, whereby the particulate material is being withheld within the tube, by the means to withhold said particles whilst the liquid is collected in the lower cap. This is, effectively, a convenient way of separating the particles from the liquid within a dispersion.

Figure 10:
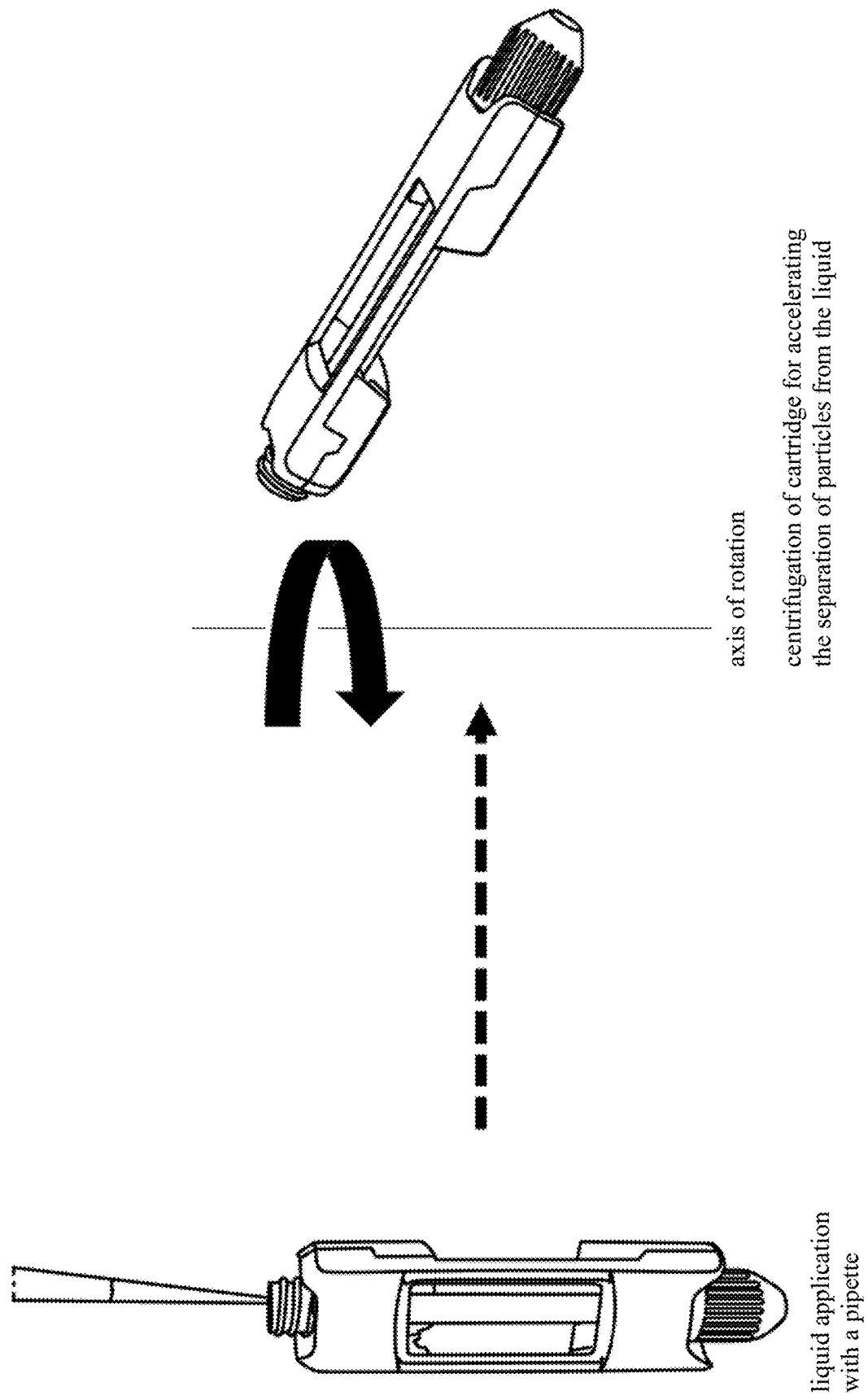

FIG. 10 shows a similar embodiment as in FIG. 8 but also demonstrates that the sample cartridge may be centrifuged after a dispersion of particles has been applied to the tube. Such centrifugation accelerates the separation of particles from the liquid. Subsequently, the lower screw cap of the tube which contains the liquid which has passed through the filter, is removed, and the liquid may be discarded or otherwise handled. The clamp at the end opposite the means to withhold (e. g. filter) is lowered and thus the tube is closed at such end. Subsequently, the cartridge may be positioned up-side-down with respect to its previous orientation and further centrifuged, as a result of which the particles are removed from the filter and transferred back into the interior space of the tube where they may be further re-suspended in another liquid such as a non-aqueous liquid and accumulated at the closed clamp end of the tube. Subsequently, the sample cartridge may be introduced into a device for incubating a dispersion of particles . . . , etc. in accordance with the present invention that is equipped with means e.g. a temperature controlling unit/surface to press the tube against a transparent planar substrate which forms part of the sample cartridge and acts as a counter surface. The tube is pressed against said surface by moving such means to press against the tube. Such means may for example be a temperature controlling unit having a temperature controlling surface which is adapted to heat or cool via said temperature controlling surface. To adjust the appropriate height of the interior space of the tube, there may be provided predefined spacer(s) located on the counter unit or on the temperature controlling unit or both. Depending on the amount of pressure exerted, the height of the spacer(s), the particles within the tube may be arranged in any desired manner, for example, a monolayer of particles maybe established. Thereafter, a desired biochemical reaction or incubation may take place; for example a thermal incubation step or several of said steps may be performed, and such step(s) may lead to an optically detectable signal on or within the particles which may then subsequently be analyzed by for example optically scanning the tube and detecting the generated signals, using optical detection means.

FIG. 11 shows a light transmission image of spread particles with a particle diameter of approximately 35 µm (panel a); panel b shows the fluorescence image of a compressed tube with spread particles after temperature incubation steps, e. g. thermal cycling. The size of the image is 2×6 cm$^2$; at the left side of the image, the clamp area can be seen.

Figure 12:
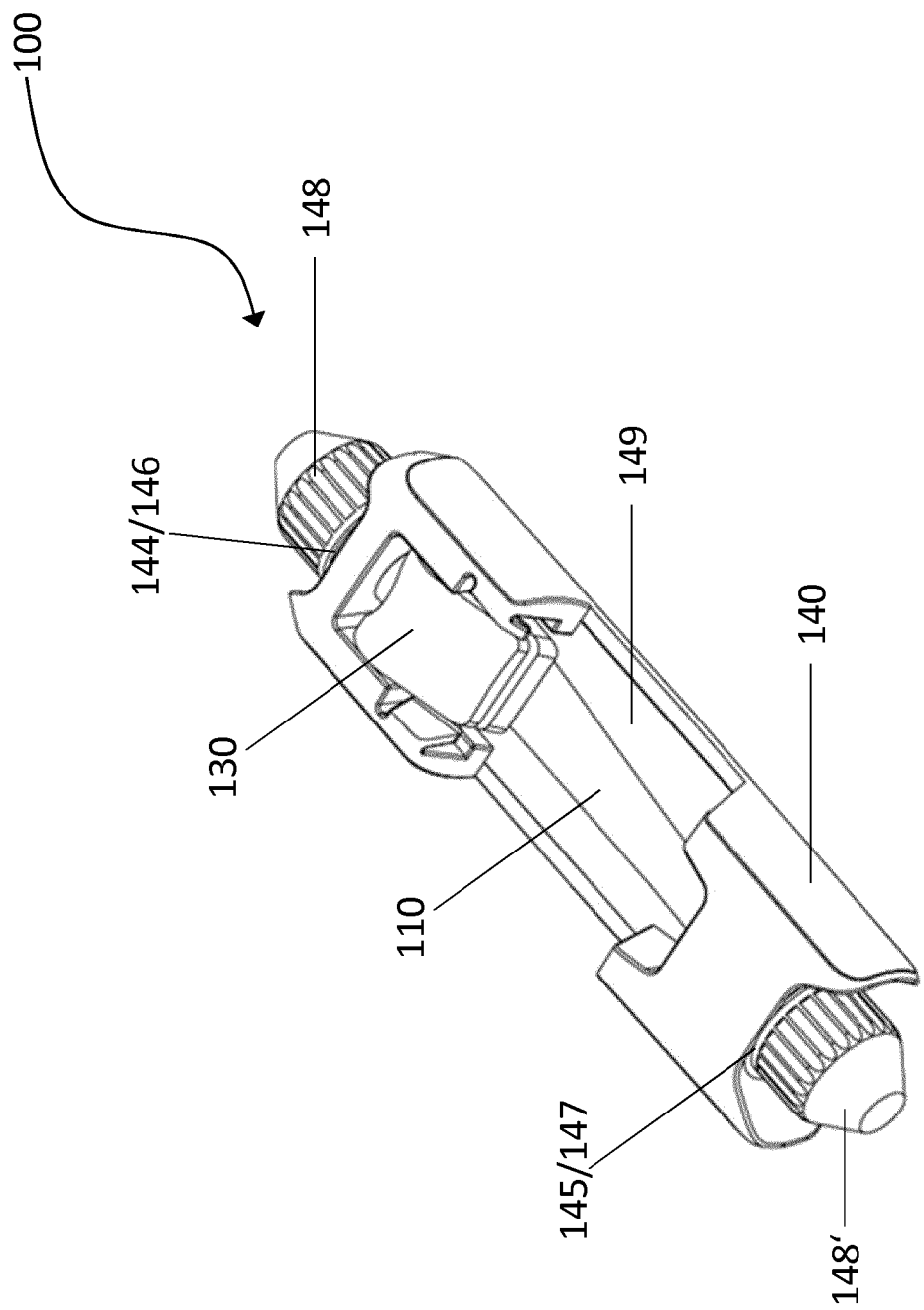
Figure 12:
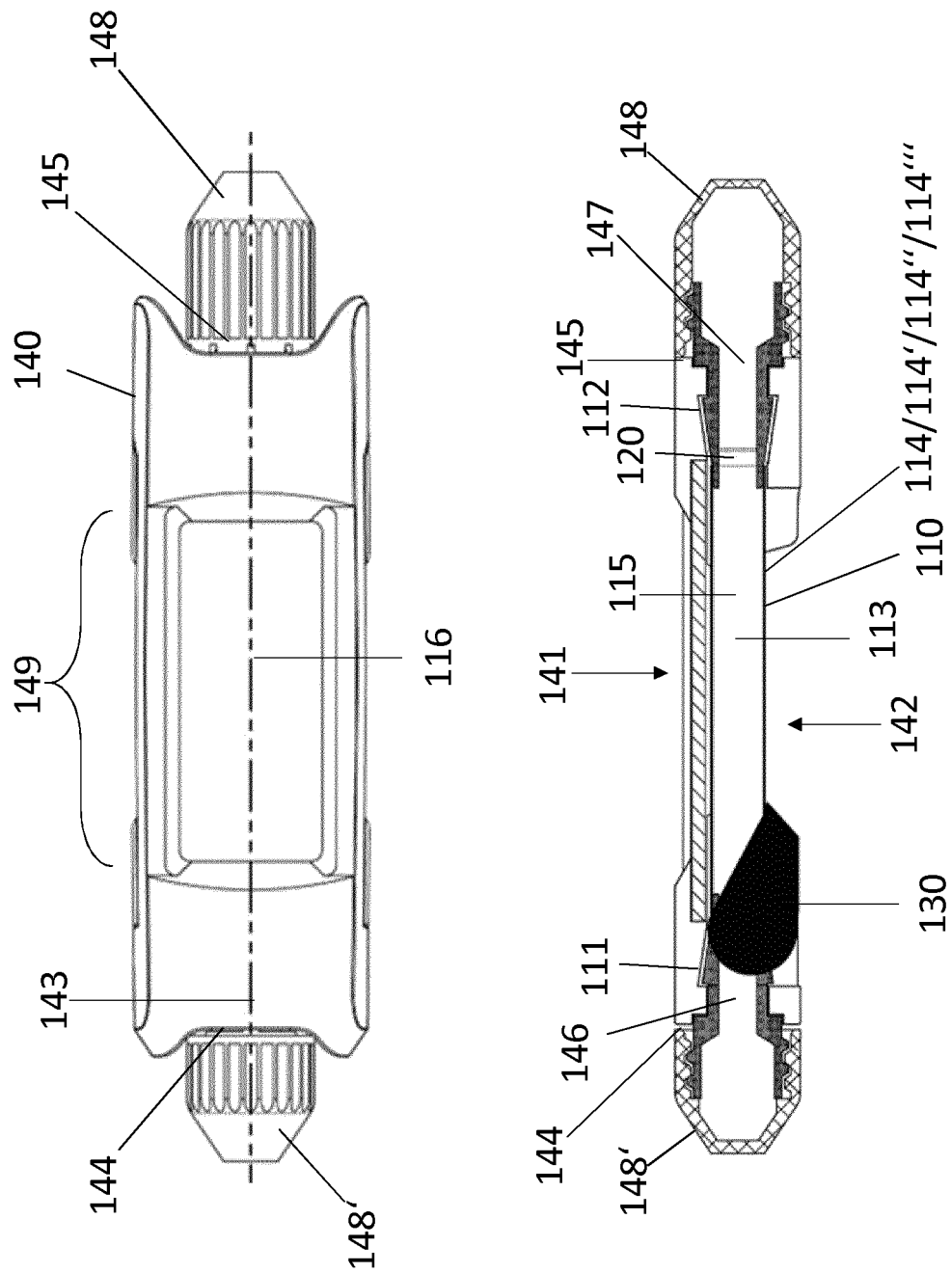
Figure 12:
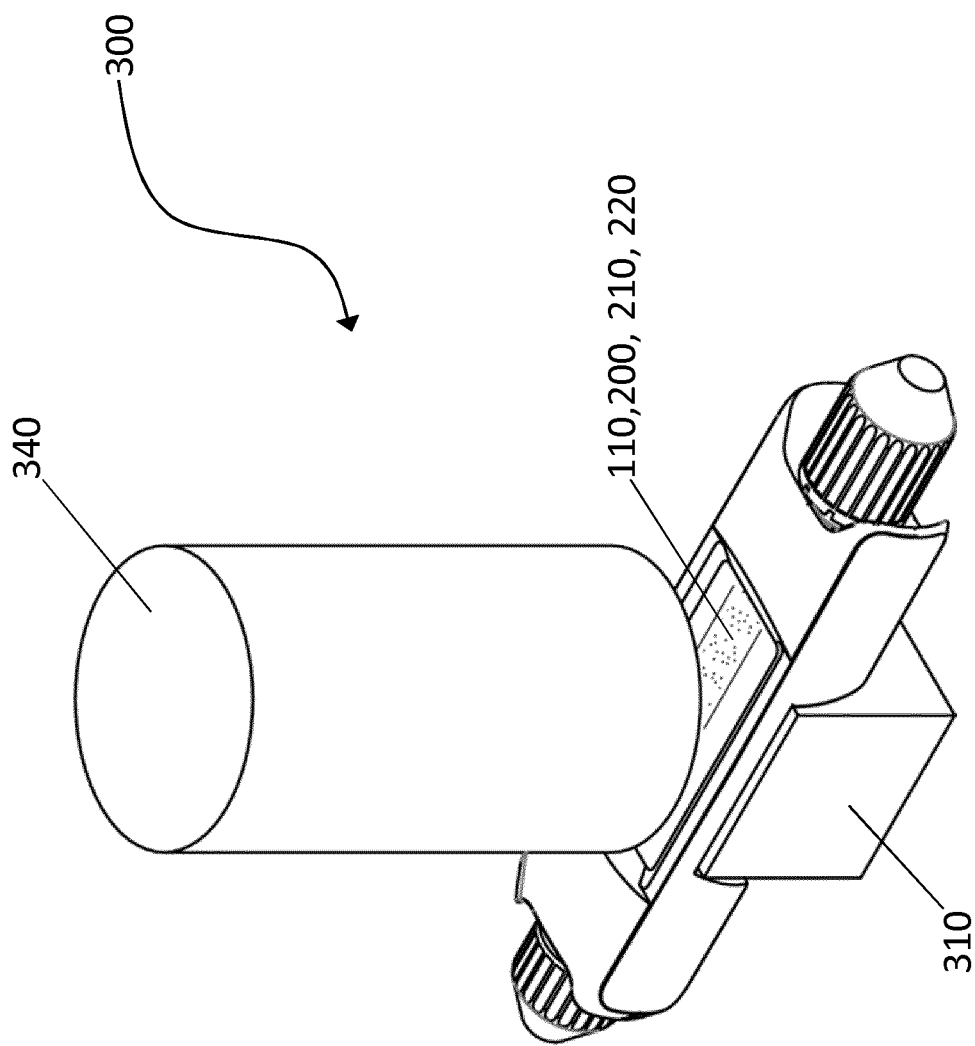

FIG. 12 shows an embodiment of a sample cartridge according to the present invention wherein panel a shows a side view, panel b a top view and a cross-sectional side view and panel c a side view of a sample cartridge, wherein in panel c, there are also shown parts of an embodiment of a device for incubating a dispersion of particles, cells or droplets, including a temperature controlling unit and optical detection means. Reference signs have been included.

LIST OF REFERENCES 100 sample cartridge
110 deformable transparent tube
111/112 two oppositely located ends of tube
113 interior space of tube
114/114'/114" one or several walls of tube
114''' single wall of tube
115 central portion of tube
116 longitudinal axis of tube
120 means to withhold
130 means to reversibly close and seal tube
140 mounting frame
141/142 first and second lateral side of mounting frame
143 longitudinal axis of mounting frame
144/145 two oppositely located longitudinal ends of mounting frame
146/147 orifices located at longitudinal ends 144/145, respectively
148/148' means to reversibly close and seal orifices 146/147, respectively
149 space encompassed by mounting frame
200 dispersion of particles, cells or droplets
210 suspension of particles or cells
220 emulsion of droplets
300 device for incubating
310 temperature controlling unit
311 temperature controlling surface
312 receiving portion for tube
320 counter unit
321 counter surface
330/330' one or several spacers
340 optical detection means The features of the present invention disclosed in the specification, the claims, and/or in the accompanying drawings may, both separately and in any combination thereof, be material for realizing the invention in various forms thereof.

The invention claimed is:

1. A sample cartridge for incubating and/or analyzing a dispersion of particles, cells or droplets, and/or for performing biochemical reactions with or in such dispersion, said cartridge comprising:

a deformable transparent unbranched tube having a single interior space, a longitudinal axis and two oppositely located open ends serving as an inlet and an outlet, respectively, wherein said oppositely located open ends of said tube are arranged such that they are aligned with each other and along said longitudinal axis;

said tube being adapted to receive a dispersion of particles, cells or droplets, in said single interior space of said tube, said single interior space being lined by one or several walls of said tube, wherein the tube is configured such that the single interior space of said tube, when having received said dispersion, has a circular or oval cross-section, such that the single interior space, when the tube is pressed against a surface, has a flat, noncircular cross-section;

said cartridge further comprising:

means to withhold said particles, cells or droplets in said deformable transparent tube, said means to withhold said particles, cells or droplets being located at one or both ends of said tube, said means to withhold being a filter, a membrane, a grid, a mesh or a sieve, allowing the passage of liquid through it whilst retaining said particles, cells or droplets; and a mounting frame connected to and holding said tube at said oppositely located ends of said tube and configured to allow addition of material to said single interior space of said tube via one of said ends serving as inlet, and/or removal of material from said single interior space of said tube via one of said ends serving as an outlet;

wherein said mounting frame has a longitudinal axis that is aligned with said longitudinal axis of said tube, and wherein said mounting frame comprises two oppositely located longitudinal ends, each of such oppositely located longitudinal ends having an orifice, respectively, that is in fluid connection with said oppositely located ends of said tube serving as inlet and outlet of said tube, respectively, wherein each of said orifices is sealable, and comprises means to reversibly close and seal such orifice.

2. The sample cartridge according to claim 1, wherein said deformable transparent tube has:
a single wall;
wherein said single interior space is lined by said single wall.

3. The sample cartridge according to claim 1, further comprising:
means to reversibly close and seal said deformable transparent tube at one or both of said oppositely located ends.

4. The sample cartridge according to claim 1, wherein said mounting frame has a first and a second lateral side located opposite each other, wherein one of said lateral sides is formed by a transparent planar substrate configured to act as a counter surface against which said tube may be pressed, wherein said mounting frame is configured such that the other of said lateral sides of said mounting frame allows exposure of a central portion of said tube to a temperature controlling device by allowing physical contact of said temperature controlling device to said central portion of said tube through said other of said oppositely located lateral sides and by allowing exertion of pressure by said temperature controlling device to said central portion of said tube through said other of said oppositely located lateral sides, wherein said temperature controlling device is not a part of the sample cartridge.

5. The sample cartridge according to claim 1, wherein said mounting frame is further configured to allow analysis of a central portion of said tube by optical detection means, wherein said optical detection means does not form a part of the sample cartridge.

6. The sample cartridge according to claim 4, wherein said central portion of said tube is a portion that has been closed and sealed by said means to reversibly close and seal said deformable transparent tube.

7. The sample cartridge according to claim 1, wherein said tube is mounted in said mounting frame such that said oppositely located open ends of said tube are attached to or contact said oppositely located longitudinal ends of said mounting frame, and wherein said mounting frame encompasses a space through which said tube extends, such space being configured to allow exposure or contact of a central portion of said tube to a temperature controlling device and/or to allow analysis of a central portion of said tube by optical detection means; wherein said temperature controlling device and said optical detection means do not form parts of the sample cartridge.

8. The sample cartridge according to claim 1, wherein said wall of said tube has a thickness in a range of from 1 μm to 1000 μm and/or wherein the diameter of said interior space, when having a circular or oval cross-section, is in the range of from 0.1 cm to 5 cm, and/or wherein a height of said interior space of said tube, when having a flat, noncircular cross-section, is in a range of from 5 μm to 500 μm wherein, said deformable transparent tube is made of a material which is transparent in or within a range of from 250 nm to 950 nm and which allows an analysis of any content, if present, within said interior space of said tube by means of optical spectroscopy and/or imaging, wherein said material is selected from styrene-butadiene-rubber, silicone-rubber, polyvinyl butyral, polyurethane, polyisobutylene, polyhydroxybutyrate, polyhydroxyalkanoate, polyether-block-amide, rubber, gummi arabicum, isoprene-rubber, fluoro-rubber, ethylene-vinylacetate-copolymer, ethylene-propylenediene-rubber copolymer, ethylene-ethylacrylate-copolymer, chloroprene-rubber, ethyl-rubber, butadiene-rubber, acrylonitrile-methylmethacrylate-copolymer, acrylonitrile-chlorinate-polyethylene-styrene-copolymer, acrylonitrile-butadiene-acrylate-copolymer, polyester (PES), polyethylene terephthalate (PET), polyethylene (PE), high-density polyethylene (HDPE), polyvinyl chloride (PVC), polyvinylidene chloride (PVDC), low-density polyethylene (LDPE), polypropylene (PP), polystyrene (PS), high impact polystyrene (HIPS), polyamides (PA), acrylonitrile butadiene styrene (ABS), polyethylene/acrylonitrile butadiene styrene (PE/ABS), polycarbonate (PC), polycarbonate/acrylonitrile butadiene styrene (PC/ABS), polyurethane (PU), and combination of any the foregoing or its copolymers.

9. A method for the use for generating and/or processing a dispersion of particles, cells or droplets wherein said method comprises the use of a sample cartridge according to claim 1.

10. The method according to claim 9, wherein said processing is one or several of the following activities: incubating said dispersion of particles, cells or droplets, performing a biochemical reaction with said dispersion of particles, cells or droplets, binding one or several analytes to said particles, cells or droplets and thereafter removing any unbound analytes and other unbound material from said particles, cells or droplets, exchanging a liquid phase of said dispersion, and analysing said dispersion of particles, cells or droplets.

11. The method according to claim 9, wherein said use comprises filling a dispersion of particles, cells or droplets, and, optionally, one or several additional reagents into said tube;
optionally, arranging said particles, cells or droplets in a monolayer;
performing a biochemical reaction within said tube and/or incubating said tube at one or several defined reaction conditions; and
analyzing the results of such biochemical reaction and/or of such incubation.

12. The method according to claim 9, wherein said use comprises:
filling a dispersion of particles, cells or droplets, into said tube, said dispersion comprising a first liquid;
removing said first liquid from said particles, cells or droplets in said tube whilst said particles, cells or droplets are withheld by said means to withhold;
adding a second liquid containing an analyte to said tube;
incubating said particles, cells or droplets in said second liquid to allow or facilitate binding of said analyte to said particles, cells or droplets;
removing said second liquid from said particles, cells or droplets in said tube whilst said particles, cells or droplets are withheld by said means to withhold;
optionally washing said particles, cells or droplets in order to remove any unbound analytes and unbound material from said particles, cells or droplets;
resuspending particles in a third liquid by adding such third liquid to said tube;
optionally, arranging said particles, cells or droplets in a monolayer;
performing a biochemical reaction within said tube and/or incubating said tube at one or several defined reaction conditions; and
analyzing the results of such biochemical reaction and/or of such incubation.

13. A method of generating a dispersion of droplets, said method comprising the steps:
providing a cartridge according to claim 1, mixing, within the tube of said cartridge, an aqueous phase and an oily liquid phase, thus generating a dispersion of droplets.

14. A method of generating a dispersion of a solid or semi-solid, said method comprising the steps: providing a cartridge according to claim 1, mixing, within the tube of said cartridge, an aqueous phase and an oily liquid phase, thus generating a dispersion, wherein one of said phases additionally contains either solid particles or one or several components capable of forming a gel or a solid upon changing at least one environmental condition around said component, wherein, if one of said phases additionally contains one or several components capable of forming a gel or solid, said method additionally comprises the step of inducing the formation of a gel or of a solid by changing said at least one environmental condition around said component, thereby converting said droplets into particles and generating a dispersion of particles within said tube.

15. A device for incubating a dispersion of particles, cells or droplets, and/or for performing a biochemical reaction therewith, said device comprising:
a sample cartridge according to claim 1;
a temperature controlling unit (310) having a temperature controlling surface and being adapted to heat and/or cool via said temperature controlling surface;
wherein the device is configured such that said tube of said sample cartridge, can be brought or is in contact with said temperature controlling surface by way of one of said lateral sides and can be or is pressed by or against said temperature controlling surface, whereby said tube, when pressed by or against said temperature controlling surface, is deformed and wherein said interior space of said pressed tube has a flat, non-circular cross-section.

16. The device according to claim 15, further comprising:
a counter unit located opposite said temperature controlling unit at a distance therefrom and having a counter surface facing said temperature controlling surface, wherein said counter unit either is said transparent planar substrate, if present in said cartridge, forming one of said lateral sides of said cartridge and configured to act as a counter surface against which said tube may be pressed, or said counter unit is a separate component not forming part of the cartridge and being provided in said device separate from said cartridge, said separate component being configured to be operable so as to exert pressure via said counter surface on said tube that is in contact with said temperature controlling surface or being operable to be positioned at a defined distance to said sample cartridge.

17. The device according to claim 16, wherein either the temperature controlling surface or the counter surface is transparent or both in a range of from 250 nm to 950 nm.

18. The device according to claim 15, further comprising optical detection means, said optical detection means being configured to be capable of detecting and/or analyzing the content of said interior space of said tube by means of optical spectroscopy and/or imaging, wherein such detection and/or analysis is performed with a beam path going through a central portion of said tube, and either said temperature controlling surface or said counter surface or both.

19. A method of use of the device according to claim 15 for generating and/or processing a dispersion of particles, cells or droplets.

* * * * *